(12) United States Patent
Charrier et al.

(10) Patent No.: US 7,909,889 B2
(45) Date of Patent: Mar. 22, 2011

(54) LIGHTENING AND/OR COLORING HUMAN KERATIN FIBERS USING AT LEAST ONE AMINOTRIALKOXY SILANE OR AT LEAST ONE AMINOTRIALKENYLOXY SILANE COMPOSITION

(75) Inventors: Delphine Charrier, Paris (FR); Marie-Pascale Audousset, Asnieres (FR); Leila Hercouet, Neuilly Plaisance (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/770,115

(22) Filed: Apr. 29, 2010

(65) Prior Publication Data

US 2010/0275387 A1    Nov. 4, 2010

Related U.S. Application Data

(60) Provisional application No. 61/176,207, filed on May 7, 2009, provisional application No. 61/176,593, filed on May 8, 2009, provisional application No. 61/179,844, filed on May 20, 2009.

(30) Foreign Application Priority Data

Apr. 30, 2009   (FR) ..................... 09 52914
Apr. 30, 2009   (FR) ..................... 09 52931
Apr. 30, 2009   (FR) ..................... 09 52934

(51) Int. Cl.
*A61Q 5/10* (2006.01)
*A61K 8/89* (2006.01)

(52) U.S. Cl. ............. 8/405; 8/406; 8/410; 8/411; 8/431; 8/435; 8/501; 8/521; 8/581; 8/582; 8/632; 132/202; 132/208; 424/70.12

(58) Field of Classification Search ............. 8/405, 410, 8/411, 431, 435, 501, 521, 581, 582, 632; 132/202, 208; 424/70.12

See application file for complete search history.

(56) References Cited

U.S. PATENT DOCUMENTS

| 6,190,421 | B1 | 2/2001 | Rondeau et al. |
| 6,554,870 | B1 | 4/2003 | Cotteret et al. |
| 6,730,133 | B1 | 5/2004 | Plos et al. |
| 2004/0060127 | A1 | 4/2004 | Sabelle et al. |
| 2006/0110351 | A1* | 5/2006 | Koehler et al. ............ 424/70.12 |

FOREIGN PATENT DOCUMENTS

| EP | 0 673 641 A1 | 9/1995 |
| EP | 1 086 684 A1 | 3/2001 |
| EP | 1 375 480 A1 | 1/2004 |
| EP | 1 767 187 A2 | 3/2007 |
| EP | 1 767 189 A2 | 3/2007 |
| WO | WO 97/39727 | 10/1997 |
| WO | WO 2004/012691 A1 | 2/2004 |
| WO | WO 2009/056779 A2 | 5/2009 |

OTHER PUBLICATIONS

STIC Search Report dated Sep. 29, 2010.*
French Search Report for FR 0952914, dated Dec. 18, 2009.
English language abstract of EP 1 767 187 A2, Mar. 28, 2007.
English language abstract of EP 1 767 189 A2, Mar. 28, 2007.

* cited by examiner

*Primary Examiner* — Eisa B Elhilo
(74) *Attorney, Agent, or Firm* — Finnegan, Henderson, Farabow, Garrett & Dunner, LLP

(57) ABSTRACT

The present invention provides a method of lightening and/or coloring human keratin fibers that employs: at least one substantially anhydrous or aqueous composition (A) comprising at least one fat free of carboxylic acid groups and at least one surfactant, at least one substantially anhydrous or aqueous composition (B) comprising at least one specific aminotrialkoxysilane or aminotrialkenyloxysilane compounds, and at least one aqueous composition (C) comprising at least one oxidizing agent. In addition, the present invention provides a three-compartment device appropriate for the implementation of this method.

15 Claims, No Drawings

LIGHTENING AND/OR COLORING HUMAN KERATIN FIBERS USING AT LEAST ONE AMINOTRIALKOXY SILANE OR AT LEAST ONE AMINOTRIALKENYLOXY SILANE COMPOSITION

This application claims benefit of U.S. Provisional Application No. 61/176,207, filed May 7, 2009, U.S. Provisional Application No. 61/176,593, filed May 8, 2009, and U.S. Provisional Application No. 61/179,844, filed May 20, 2009. This application also claims benefit of priority under 35 U.S.C. §119 to French Patent Application Nos. 0952914, 0952931, and 0952934, filed Apr. 30, 2009.

Disclosed herein is a method of lightening and/or coloring human keratin fibers comprising, at least one oxidizing agent, at least three additional compositions, wherein at least one is substantially anhydrous or aqueous and comprises at least one aminotrialkoxy silane or aminotrialkenyloxy silane compound.

In addition, embodiments of the invention disclosed herein relate to a device comprising at least three compartments.

The techniques for coloring human keratin fibers such as the hair include permanent or oxidation dyeing. Permanent or oxidation dyeing may include, at least one oxidation dye precursor, for example, at least one oxidation base optionally in combination with at least one coupler.

The at least one oxidation base may be chosen from ortho- or para-phenylenediamines, ortho- or para-aminophenols, and heterocyclic compounds. These oxidation bases are colorless or weakly colored compounds which, in combination with oxidizing products, provide access to colored species by a process of oxidative condensation.

The shades obtained with the at least one oxidation base may be varied by combining them with at least one coupler, the at least one coupler chosen from aromatic meta-diamines, meta-aminophenols, meta-diphenols, and certain heterocyclic compounds, such as indole compounds.

The variety of at least one oxidation base and at least one coupler may allow a rich palette of colors to be obtained.

One coloring method comprises contacting at least one oxidation dye precursor with at least one oxidizing agent, for example hydrogen peroxide, under alkaline conditions. A commonly used alkaline agent is aqueous ammonia, which can be used to adjust the pH of the composition to an alkaline pH to allow the breakdown of the oxidizing agent. The oxygen formed causes condensation of the at least one oxidation dye precursor and lightening of fiber via breakdown of melanin. The alkaline agent further may swell the keratin fiber in order to promote the penetration of the at least one oxidizing agent and any dyes to the interior of a fiber.

Alkaline agents may be highly volatile, and may cause unpleasantness to the user due to the strong and fairly unpleasant odor of ammonia that is given off during the procedure.

Moreover, the use of greater ammonia levels than necessary may be required in order to compensate for the amount of ammonia given off. This may increase the risk of user intolerance, such as, for example, irritation of the scalp, for example, stinging sensations.

Replacing all or some of the aqueous ammonia by other conventional alkaline agents does not result in compositions that are as effective as those based on aqueous ammonia, for example, other alkaline agents may not provide sufficient lightening of pigmented fibers in the presence of at least one oxidizing agent.

Another coloring method is direct or semi-permanent dyeing. This method comprises applying direct dyes to keratin fibers, wherein the dyes are colored and wherein coloring molecules have an affinity for the fibers, leaving the direct dyes on the keratin fibers, allowing the molecules to penetrate by diffusion to the interior of the fiber, and rinsing the fibers.

Direct dyes may be chosen from nitrobenzene, anthraquinone-based, nitropyridine, azo, methine, azomethine, xanthene, acridine, azine and triarylmethane direct dyes.

This coloring method optionally comprises the use of an oxidizing agent to lighten the fiber at the same time as coloring it. If optionally comprising an oxidizing agent, the procedure is the same as oxidation dyeing, comprising contacting the keratin fibers with the dyeing composition in the presence of an oxidizing agent, for example, hydrogen peroxide, under alkaline conditions, generally in the presence of aqueous ammonia. The user, consequently, is then confronted once again with the same difficulties as those set out above for oxidation dyeing.

In addition to coloring procedures, lightening procedures, may comprise contacting keratin fibers with at least one oxidizing composition under alkaline conditions. Lightening procedures involve breaking down the melanin in the hair, to a greater or lesser extent depending on the oxidizing agent selected. For example, using a peroxygenated salt may lead to a greater lightening than when using hydrogen peroxide alone under alkaline conditions. Irrespective of the oxidizing agent employed, however, lightening procedures require the use of hydrogen peroxide under alkaline conditions, such as in the presence of aqueous ammonia, to form or accelerate the formation of oxygen. Consequently, the same difficulties are encountered as those with coloring procedures employed in the presence of an oxidizing agent and aqueous ammonia.

Disclosed herein are coloring and lightening compositions for human keratin fibers for use with at least one oxidizing agent, but which do not have the same drawbacks described above, owing to the presence of large amounts of aqueous ammonia, while remaining at least equally effective, from the standpoints both of lightening and of coloring, and which may display, high performance in terms of chromaticity, power and homogeneity.

The present disclosure, therefore provides a method of coloring and/or lightening human keratin fibers, comprising contacting fibers with:

at least one substantially anhydrous or aqueous composition (A) comprising at least one fat free of carboxylic acid groups and at least one surfactant, at least one substantially anhydrous or aqueous composition (B) comprising at least one organosilicon compound chosen from silanes comprising a silicon atom and siloxanes comprising two or three silicon atoms, the at least one organosilicon compound further comprising at least one basic chemical function and at least one hydroxyl or hydrolysable groups per molecule, and at least one aqueous composition (C) comprising at least one oxidizing agent.

The at least one organosilicon compounds are chosen from organosilanes comprising a silicon atom and organosiloxanes comprising two or three silicon atoms, for example, two silicon atoms. They further comprise at least one basic chemical function, for example one basic chemical function. The at least one basic chemical function may correspond to any function that gives the silicon compound a basic nature, such as, for example an amine function such as a primary, secondary or tertiary amine function. The at least one basic chemical function of the silicon compounds may optionally comprise other functions, for example another amine function, an acid function or a halogen function.

In one embodiment, the at least one organosilicon compound further comprises at least two hydrolysable or hydroxyl groups per molecule. The hydrolysable groups may be chosen from, for example, alkoxy, aryloxy and halogen groups. They may further optionally comprise other chemical functions such as acid functions.

The at least one organosilane compound may be chosen from the compounds of formula (II):

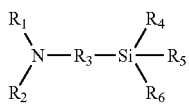
(II)

wherein:

$R_4$ is chosen from a halogen, a group OR' and R'$_1$;

$R_5$ is chosen from a halogen, a group OR'' and R'$_2$;

$R_6$ is chosen from a halogen, a group OR''' and R'$_3$;

$R_1$, $R_2$, $R_3$, R', R'', R''', R'$_1$, R'$_2$ and R'$_3$ are chosen from, independently of each other, a saturated or unsaturated, linear or branched hydrocarbon-based group, optionally bearing additional chemical groups, $R_1$, $R_2$, R', R'' and R''' which may optionally be hydrogen, and at least two of the $R_4$, $R_5$ and $R_6$ may be chosen from, OR', OR'' and OR''', wherein at least two of the groups R', R'' and R''' are not hydrogen.

According to one embodiment, the groups $R_1$, $R_2$, R', R'$_1$, R'$_2$, R'$_3$, R'' and R''' are chosen from $C_1$-$C_{12}$ alkyl, $C_6$-$C_{14}$ aryl, $C_1$-$C_8$-alkyl-$C_6$-$C_{14}$-aryl and $C_6$-$C_{14}$-aryl-$C_1$-$C_8$-alkyl radicals.

The at least one organosiloxanes may be chosen from the compounds of formula (III):

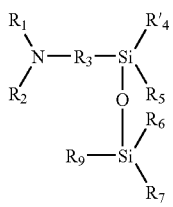
(III)

wherein:

$R_1$, $R_2$, $R_3$, $R_5$ and $R_6$, are as defined above;

R'$_4$ is chosen from a halogen atom and a group OR$_{11}$;

$R_7$ is chosen from a halogen atom, a group OR$_{10}$ and R''$_1$;

$R_9$ is chosen from a halogen atom, a group OR$_8$, R''$_2$ and $R_3$NR$_1$R$_2$;

R''$_1$, R''$_2$, $R_8$, $R_{10}$ and $R_{11}$ are chosen from a linear or branched, saturated or unsaturated hydrocarbon-based group optionally bearing additional chemical groups, the groups $R_{11}$, $R_{10}$ and $R_8$ may optionally be hydrogen; at least one of the groups $R_6$, $R_7$, and $R_9$ are chosen from a halogen atom, a group OR''', OR$_{10}$ and OR$_8$.

In at least one embodiment, the groups R''$_1$, R''$_2$, $R_8$ or $R_{10}$ and $R_{11}$ are chosen from $C_1$-$C_{12}$ alkyl, $C_6$-$C_{14}$ aryl, $C_1$-$C_8$-alkyl-$C_6$-$C_{14}$-aryl and $C_6$-$C_{14}$-aryl-$C_1$-$C_8$-alkyl radicals.

In another embodiment, the halogen atom is a chlorine atom.

The at least one organosilicon compound may be chosen from the compounds of formula (IV):

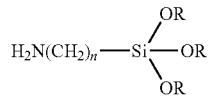
(IV)

wherein the radicals R, which may be identical or different, are chosen from $C_1$-$C_6$, for example, $C_1$-$C_2$ alkyl radicals and wherein n is an integer chosen from 1 to 6, for example, chosen from 2 to 4.

In at least one embodiment, the silanes or siloxanes are water-soluble, for example soluble to a concentration of 2%, further for example to a concentration of 5% and further for example to a concentration of 10% by weight in water at a temperature of 25° C.±5° C. and at atmospheric pressure. The term "soluble" means the formation of a single macroscopic phase.

According to at least one embodiment, the at least one organosilicon compound is chosen from the compounds of formula (I) below:

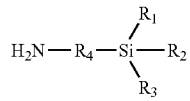

wherein:

$R_1$, $R_2$ and $R_3$, which may be identical or different, are chosen from:

a linear or branched $C_1$-$C_{20}$ alkoxy radical wherein the alkyl moiety is optionally interrupted with one or more oxygen atoms, and a linear or branched $C_2$-$C_{20}$, such as $C_2$-$C_4$, alkenyloxy radical, $R_4$ is a divalent radical of structure:

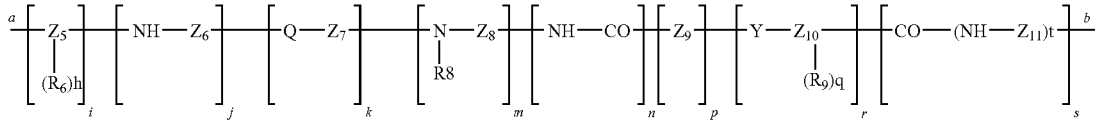

wherein $R_6$, may be identical or different at each occurrence, and is chosen from a linear or branched $C_1$-$C_4$ alkyl radical, such as methyl or ethyl, optionally substituted with one or more hydroxyl groups, an NH$_2$ radical, a hydroxyl radical, a cyano radical, a radical $Z_{12}$NH$_2$, a radical $Z_{13}$NH $Z_{14}$NH$_2$, and a linear or branched $C_2$-$C_{10}$, such as a $C_2$-$C_4$, alkenyl radical, with $Z_{12}$, $Z_{13}$ and $Z_{14}$ being chosen from, independently of each other, a $C_1$-$C_{20}$, such as $C_1$-$C_{10}$, or a $C_1$-$C_4$, linear alkylene radical $R_8$ is chosen from a linear or branched $C_1$-$C_4$ alkyl radical, such as methyl or ethyl, optionally substituted with one or more hydroxyl or carboxyl groups, a linear or branched $C_2$-$C_{10}$, such as $C_2$-$C_4$, alkenyl radical, a radical $Z_{15}NH_2$, a radical $Z_{16}R_8'$ and a radical $Z_{17}Si\ OSi(R_a)_2(R_b)$ wherein $R_a$ is a linear or branched $C_1$-$C_4$ alkoxy radical, such as methoxy or ethoxy $R_b$ is a linear or branched $C_1$-$C_4$ alkyl radical, such as methyl or ethyl $Z_{15}$, $Z_{16}$ and $Z_{17}$ are, independently of each other, a $C_1$-$C_{20}$, such as $C_1$-$C_{10}$ or $C_1$-$C_4$, linear alkylene radical $R_8'$ is a $C_6$-$C_{30}$ aryl radical, such as phenyl $R_9$ is a linear or branched $C_1$-$C_4$ alkyl radical $Z_5$, $Z_6$, $Z_6$, $Z_7$, $Z_8$, $Z_9$, $Z_{10}$ and $Z_{11}$ are, independently of each other, a $C_1$-$C_{20}$ linear alkylene radical Q is a saturated or unsaturated six-membered ring optionally comprising one or more heteroatoms Y, may be identical or different at each occurrence, and is chosen from an oxygen atom, a sulfur atom and an NH group h is an integer chosen from 0, 1, 2, 3, 4 and 5 i is an integer chosen from 0 and 1 j is an integer chosen from 0, 1, 2 and 3 k is an integer chosen from 0 and 1 m is an integer chosen from 0 and 1 n is an integer chosen from 0 and 1 p is an integer chosen from 0 and 1 q is an integer chosen from 0 and 1 r is an integer chosen from 0, 1, 2 and 3 s is an integer chosen from 0 and 1 wherein at least one of the coefficients h, i, j, k, m, n, p, q, r and s is non-zero a is the bond to the silicon atom b is the bond to the nitrogen atom of the amino group.

The process disclosed herein makes it possible to obtain a hair coloration with satisfactory dyeing properties, for example in terms of intensity, power, homogeneity, chromaticity and selectivity, and resistance of the color to external agents such as resistance to shampoos, sweat and bad weather.

The process disclosed herein further gives hair good styling properties such as volume and body, and a soft, smooth feel, even when it is applied to hair that has been sensitized beforehand by a chemical treatment.

Further disclosed herein is a multi-compartment device comprising in a first compartment at least one substantially anhydrous or aqueous composition (A) comprising at least one fat free of carboxylic acid groups and at least one surfactant, in a second compartment at least one substantially anhydrous or aqueous composition (B) comprising at least one organosilicon compound chosen from silanes comprising a silicon atom and siloxanes comprising two or three silicon atoms, the at least one organosilicon compound further comprising at least one basic chemical function and at least one hydroxyl or hydrolysable groups per molecule, and in a third compartment at least one aqueous composition (C) comprising at least one oxidizing agent.

Further disclosed herein is a ready-to-use composition comprising at least one organosilicon compound chosen from silanes comprising a silicon atom and siloxanes comprising two or three silicon atoms, the at least one organosilicon compound further comprising at least one basic chemical functions and at least one hydroxyl or hydrolysable groups per molecule and at least one dye, such as at least one dye precursor, at least one oxidizing agent and at least one cationic polymer and/or at least one oxyalkylenated or glycerolated nonionic surfactant.

Other features and advantages will become more clearly apparent on reading the description and examples that follow.

It should be noted that, in the text below, the endpoints encompassing a range of values are included in that range unless specifically indicated otherwise.

The human keratin fibers treated by the method are for example the hair.

Moreover, composition(s) (A) and/or (B) are substantially anhydrous or aqueous compositions.

In at least one embodiment of the present disclosure, an aqueous composition comprises greater than 5% by weight of water, for example greater than 10% by weight of water and further for example greater than 20% by weight of water.

According to at least one embodiment, when the composition(s) (A) and/or (B) are aqueous, the water content ranges from 5% to 95% by weight, for example from 25% to 90% by weight and further for example from 40% to 85% by weight relative to the weight of the composition.

According to another embodiment, when composition(s) (A) and/or (B) are aqueous, the water content ranges from 30% to 78% by weight, for example from 40% to 70% by weight and further for example from 45% to 60% by weight relative to the weight of the composition.

Composition(s) (A) and/or (B) may optionally comprise at least one organic solvent.

At least one organic solvent may be chosen from linear or branched $C_2$-$C_4$ alkanols, such as ethanol and isopropanol; glycerol; glycols and glycol ethers, for example 2-butoxyethanol, propylene glycol, dipropylene glycol, propylene glycol monomethyl ether and diethylene glycol monomethyl ether or monoethyl ether, and also aromatic alcohols, for example benzyl alcohol or phenoxyethanol, and mixtures thereof.

The at least one organic solvent may be present in an amount ranging from 1% to 40% by weight and for example from 5% to 30% by weight relative to the weight of the composition.

In at least one embodiment, a substantially anhydrous composition has a water content of less than 5% by weight, for example less than 2%, further for example less than 1%, by weight, relative to the weight of the composition. In embodiments of the present disclosure, the water may be, for example, bound water, such as water of crystallization in salts, or traces of water absorbed by the raw materials used in the production of the compositions of the disclosure.

In another embodiment, the compositions employed in the method as disclosed herein do not include ingredients which would make it or them ineligible for use in the coloring and/or lightening of human keratinous fibers Accordingly, the ingredients they comprise are cosmetically acceptable ingredients.

The at least one substantially anhydrous or aqueous composition (A) comprises at least one fat free of carboxylic acid groups and at least one surfactant.

The term "fat" is understood to mean an organic compound that is insoluble in water at standard temperature (25° C.) and at atmospheric pressure (760 mmHg) (solubility of less than 5%, for example less than 1%, further for example less than 0.1%). Under the same temperature and pressure conditions, moreover, the fats are soluble in organic solvents, such as chloroform, ethanol or benzene, for example.

In one embodiment, the fats are chosen from compounds that are liquid or pasty at ambient temperature and at atmospheric pressure.

In at least one embodiment, the fats are chosen from alkanes, fatty alcohols, fatty acid esters, fatty alcohol esters, mineral, plant, animal or synthetic oils, silicones and waxes.

For the purposes of the disclosure, fatty alcohols and esters have at least one saturated or unsaturated, linear or branched hydrocarbon group comprising 6 to 30 carbon atoms, which is optionally substituted, for example, with at least one, for example 1 to 4, hydroxyl groups. If they are unsaturated, these compounds may have one to three conjugated or non-conjugated carbon-carbon double bonds.

Alkanes may for example comprise from 6 to 30 carbon atoms and are linear. Examples may include hexane and dodecane.

As oils that may be used in the composition in embodiments of the present disclosure, non-limiting mention may for example be made of:

hydrocarbon-based oils of animal origin, such as perhydrosqualene;

hydrocarbon-based oils of plant origin, such as liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil and shea butter oil;

linear or branched hydrocarbons of mineral or synthetic origin, such as volatile or non-volatile liquid paraffins, and derivatives thereof, petrolatum, liquid petrolatum, polydecenes, hydrogenated polyisobutene such as PARLEAM®; and isoparaffins, for instance isohexadecane and isodecane;

saturated or unsaturated, linear or branched fatty alcohols comprising from 8 to 30 carbon atoms; including, for example, cetyl alcohol, stearyl alcohol and a mixture thereof (cetylstearyl alcohol), octyldodecanol, 2-butyloctanol, 2-hexyldecanol, 2-undecyl-pentadecanol, oleyl alcohol or linoleyl alcohol;

fluoro oils with partial hydrocarbon and/or silicone modification, such as those described in document JP-A-2-295912; fluoro oils also include perfluoromethyl-cyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or else bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The wax(es) may be chosen from carnauba wax, candelilla wax, esparto grass wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy raw materials such as marine waxes such as the product sold by the company Sophim under the reference M82, and polyethylene waxes or polyolefin waxes in general.

The esters may be chosen from esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Among the monoesters, non-limiting mention may, for example, be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, and 2-hexyldecyl laurate.

Further for example, esters may be chosen from esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols.

Non-limiting mention may for example be made of esters, for instance diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Esters that may for example be used are ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may further comprise, as fatty ester, sugar esters and diesters of $C_6$-$C_{30}$, for example $C_{12}$-$C_{22}$, fatty acids. The term "sugar" within the context of the present disclosure is understood to mean oxygen-bearing hydrocarbon-based compounds which contain several alcohol functions, with or without aldehyde or ketone functions, and comprise at least 4 carbon atoms. These sugars may be monosaccharides, oligosaccharides or polysaccharides.

Examples of sugars that may for example be used include sucrose (or saccharose), glucose, galactose, ribose, fucose, maltose, fructose, mannose, arabinose, xylose and lactose, and derivatives thereof, for instance alkyl derivatives, such as methyl derivatives, for instance methylgiucose.

The sugar esters of fatty acids may be chosen from the group comprising the esters or mixtures of esters of sugars described previously and of linear or branched, saturated or unsaturated $C_6$-$C_{30}$, for example $C_{12}$-$C_{22}$, fatty acids. If they are unsaturated, these compounds may comprise one to three conjugated or non-conjugated carbon-carbon double bonds.

Esters may be chosen from mono-, di-, tri-, tetraesters and polyesters, and mixtures thereof.

These esters may be selected, for example, from oleates, laurates, palmitates, myristates, behenates, cocoates, stearates, linoleates, linolenates, caprates and arachidonates, or mixtures thereof such as, oleo-palmitate, oleo-stearate and palmito-stearate mixed esters.

Non-limiting mention may also for example be made of monoesters and diesters andsucrose, glucose or methylglucose mono- or di-oleates, stearates, behenates, oleo-palmitates, linoleates, linolenates and oleostearates.

In at least one embodiment, non-limiting mention may be made for example of the product sold under the name GLU-CATE® DO by the company Amerchol, which is a methyl-glucose dioleate.

Examples of esters or mixtures of esters of sugar and of fatty acid that may also be mentioned, in a non-limiting manner, include:

the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% di-triester-polyester;

the sucrose mono-dipalmito-stearate sold by the company Goldschmidt under the name TEGOSOFT® PSE.

The silicones that may be used in the context of the compositions of the present disclosure may be chosen from volatile or non-volatile, cyclic, linear or branched silicones, which are unmodified or modified with organic groups, having a viscosity of $5\times10^{-6}$ to 2.5 m$^2$/s at 25° C., for example $1\times10^{-5}$ to 1 m$^2$/s.

In at least one embodiment, the silicones may be chosen from silicones in the form of oils, waxes, resins and gums.

In at least one embodiment, the silicone is chosen from polydialkylsiloxanes, for example polydimethylsiloxanes (PDMS), and organomodified polysiloxanes comprising at least one functional group selected from poly(oxyalkylene) groups, amino groups and alkoxy groups.

Organopolysiloxanes are described in greater detail in Walter Noll's "Chemistry and Technology of Silicones" (1968), Academic Press. They may be volatile or non-volatile.

When the organopolysiloxanes are volatile, the silicones may be chosen from those having a boiling point of ranging from 60° C. to 260° C., and for example, may be chosen from:

(i) cyclic polydialkylsiloxanes comprising from 3 to 7, for example 4 to 5 silicon atoms. Non-limiting mention may be made, for example, of octamethylcyclotetrasiloxane sold in particular under the name VOLATILE SILICONE® 7207 by Union Carbide or SILBIONE® 70045 V2 by Rhodia, decamethylcyclopentasiloxane sold under the name VOLATILE SILICONE® 7158 by Union Carbide, and SILBIONE® 70045 V5 by Rhodia, and mixtures thereof.

Non-limiting mention may also be made of, for example, cyclocopolymers of the dimethylsiloxane/methylalkylsiloxane type, such as VOLATILE SILICONE® FZ 3109 sold by the company Union Carbide, of formula:

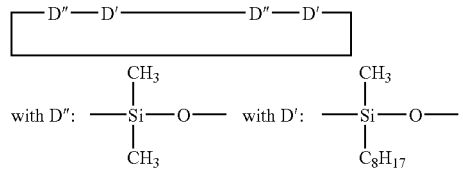

Non-limiting mention may also be made of, for example, mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes comprising from 2 to 9 silicon atoms and having a viscosity of less than or equal to $5\times10^{-6}$ m$^2$/s at 25° C. Non-limiting mention may be made, for example of decamethyltetrasiloxane sold, for example, under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

In at least one embodiment, non-volatile polydialkylsiloxanes, polydialkyl-siloxane gums and resins, polyorganosiloxanes modified with organofunctional groups above, and mixtures thereof, may be used.

In at least one embodiment, the silicones are more chosen from polydialkylsiloxanes, among which non-limiting mention may be made of, for example, polydimethylsiloxanes comprising trimethylsilyl end groups. The viscosity of the silicones is measured at 25° C. according to ASTM standard 445 Appendix C.

Among these polydialkylsiloxanes, mention may be made, in a non-limiting manner, of the following commercial products:

the SILBIONE® oils of the 47 and 70 047 series or the MIRASIL® oils sold by Rhodia, for instance the oil 70 047 V 500 000;

the oils of the MIRASIL® series sold by the company Rhodia;

the oils of the 200 series from the company Dow Corning, such as DC200 with a viscosity of 60 000 mm$^2$/s;

the VISCASIL® oils from General Electric and certain oils of the SF series (SF 96, SF 18) from General Electric.

Non-limiting mention may also be made, for example, of polydimethylsiloxanes comprising dimethylsilanol end groups known under the name Dimethiconol (CTFA), such as, for example, the oils of the 48 series from the company Rhodia.

In this category of polydialkylsiloxanes, non-limiting mention may also be made, for example, of the products sold under the names ABIL WAX® 9800 and 9801 by the company Goldschmidt, which are polydialkyl($C_1$-$C_{20}$)siloxanes.

Silicone gums that may be used in accordance with the present disclosure may be chosen from polydialkylsiloxanes, for example polydimethylsiloxanes with high number-average molecular masses ranging from 200 000 to 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, and mixtures thereof.

Silicone gums that may be used in accordance with the present disclosure are mixtures that may be chosen from:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, for example a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of 5×10$^{-6}$ m$^2$/s. This product may for example comprise 15% SE 30 gum and 85% SF 96 oil.

Organopolysiloxane resins that may be used in accordance with the present disclosure may be chosen from crosslinked siloxane systems comprising the following units:

$$R_2SiO_{2/2}, R_3SiO_{1/2}, RSiO_{3/2} \text{ and } SiO_{4/2}$$

wherein R represents an alkyl comprising from 1 to 16 carbon atoms. For example, those wherein R is a $C_1$-$C_4$ lower alkyl group, for example methyl.

In at least one embodiment, non-limiting mention may be made, for example of organopolysiloxane resins including the product sold under the name Dow Corning 593 or those sold under the names Silicone Fluid SS 4230 and SS 4267 by the company General Electric, which are silicones of dimethyl/trimethyl siloxane structure.

Non-limiting mention may also be made of, for example, trimethyl siloxy-silicate type resins sold, for example, under the names X22-4914, X21-5034 and X21-5037 by the company Shin-Etsu.

The organomodified silicones that may be used in accordance with the present disclosure are silicones as defined above and comprising in their structure at least one organofunctional groups attached via a hydrocarbon group.

In at least one embodiment, the organomodified silicones may be chosen from polydiarylsiloxanes, for example polydiphenylsiloxanes, and polyalkylarylsiloxanes functionalized with the organofunctional groups mentioned previously.

The polyalkylarylsiloxanes may be chosen from linear and/or branched polydi-methyl/methylphenylsiloxanes and polydimethyl/diphenylsiloxanes with a viscosity ranging from 1×10$^{-5}$ to 5×10$^{-2}$ m$^2$/s at 25° C.

Among these polyalkylarylsiloxanes, examples that non-limiting mention may be made of include the products sold under the following names:

the SILBIONE® oils of the 70 641 series from Rhodia;
the oils of the RHODORSIL® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, non-limiting mention may be made of, for example, polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the ($C_{1-2}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, for example, $C_1$-$C_4$ aminoalkyl groups;

alkoxylated groups such as the product sold under the name Silicone Copolymer F-755 by SWS Silicones, and ABIL WAX® 2428, 2434 and 2440 by the company Goldschmidt.

In at least one embodiment, the fat is a compound that is liquid at a temperature of 25° C. and at atmospheric pressure.

In at least one embodiment, the fat may be chosen from liquid petrolatum, liquid paraffin, polydecenes, fatty acid esters, for example those that are liquid, or mixtures thereof, and further for example liquid petrolatum, liquid paraffin and fatty acid esters, and mixtures thereof.

The at least one substantially anhydrous or aqueous composition (A) may comprise a fat content ranging from 10% to 99% by weight, relative to the weight of the composition; for example ranging from 20% to 90% by weight, further for example ranging from 25% to 80%, for example ranging from 30% to 70% by weight.

The at least one substantially anhydrous or aqueous composition (A) may further comprise at least one surfactant.

The at least one surfactant may be chosen from nonionic surfactants and anionic surfactants.

The anionic surfactants may be chosen from the salts, for example alkali metal salts, such as sodium salts, ammonium salts, amine salts, amino alcohol salts or alkaline-earth metal salts such as magnesium salts, of the following compounds:

alkyl sulfates, alkyl ether sulfates, alkylamido ether sulfates, alkylaryl polyether sulfates, monoglyceride sulfates;
alkylsulfonates, alkylamidesulfonates, alkylarylsulfonates, α-olefinsulfonates, paraffinsulfonates;
alkyl phosphates, alkyl ether phosphates;
alkylsulfosuccinates, alkyl ether sulfosuccinates, alkylamidesulfosuccinates;
alkylsulfosuccinamates;
alkylsulfoacetates;
acylsarcosinates; acylisethionates and N-acyltaurates;
salts of fatty acids such as oleic acid, ricinoleic acid, palmitic acid or stearic acid, coconut oil acid or hydrogenated coconut oil acid;
alkyl-D-galactoside uronic acid salts;
acyllactylates;
salts of polyoxyalkylenated alkyl ether carboxylic acids, of polyoxyalkylenated alkylaryl ether carboxylic acids or of polyoxyalkylenated alkylamido ether carboxylic acids, for example those comprising from 2 to 50 ethylene oxide groups;
and mixtures thereof.

In at least one embodiment, the alkyl or acyl radical of these various compounds may comprise from 6 to 24 carbon atoms, for example from 8 to 24 carbon atoms, and the aryl radical may be chosen from a phenyl and benzyl group.

The nonionic surfactants may be chosen from monooxyalkylenated or polyoxyalkylenated, monoglycerolated or polyglycerolated nonionic surfactants.

In the context of the present disclosure, the term "oxyalkylenated or glycerolated surfactant" is understood to mean a compound comprising at least one hydrocarbon-based chain comprising at least 6 carbon atoms and at least one group having the structure $$-CH_2-(C(H)_t(CH_2R_1)_n)_q-CH_{2p}-O-$$

wherein n or p or q are independently chosen from 0 and 1, t is chosen from 1 and 2,
and $R_1$ is chosen from a hydrogen atom and a hydroxyl radical.

These groups may optionally be oxyethylenated (q=0, p=1), oxypropylenated (q=1, n=0, t=2, p=1 or q=1, t=1, n=1, $R_1$=H) or glycerolated (q=1, n=0, t=2, p=1 or q=1, t=1, n=1, $R_1$=OH).

The oxyalkylene units may be chosen from, for example, oxyethylene units, oxypropylene units, and a combination thereof, for example oxyethylene units.

Examples of oxyalkylenated nonionic surfactants may include:

oxyalkylenated ($C_8$-$C_{24}$)alkylphenols, for example oxyalkylenated ($C_8$-$C_{18}$) alkylphenols, saturated or unsaturated, linear or branched, oxyalkylenated, for example $C_8$-$C_{30}$ fatty alcohols, saturated or unsaturated, linear or branched, oxyalkylenated, for example $C_8$-$C_{30}$ fatty amides, oxyalkylenated esters of saturated or unsaturated, linear or branched, for example $C_8$-$C_{30}$ fatty acids and of sucrose, esters of saturated or unsaturated, linear or branched, for example $C_8$-$C_{30}$ fatty acids and of polyethylene glycols, polyoxyethylenated esters of saturated or unsaturated, linear or branched, $C_6$-$C_{30}$, for example $C_8$-$C_{30}$ acids and of sorbitan, saturated or unsaturated, oxyethylenated plant oils, condensates of ethylene oxide and/or of propylene oxide, inter alia, alone or as mixtures.

Examples of glycerolated nonionic surfactants may include:

saturated or non-saturated, linear or branched, glycerolated, for example $C_8$-$C_{30}$ fatty alcohols, saturated or non-saturated, linear or branched, glycerolated, for example $C_8$-$C_{30}$ fatty amides, and mixtures thereof.

In at least one embodiment of the present disclosure, the average number of oxyalkylene units ranges from 2 to 150 units. For example, they may be chosen from oxyethylene-units, oxypropylene units and mixtures thereof.

In regards to the glycerolated surfactants, they may comprise on average 1 to 20, for example 1.5 to 5 glycerol groups.

According to another embodiment of the present disclosure, the at least one surfactant has a number of moles of ethylene oxide and/or of propylene oxide ranging from 1 to 90, for example, ranging from 1 to 50 and further for example, ranging from 2 to 30. In at least one embodiment of the present disclosure, the nonionic surfactants may not comprise any oxypropylene units.

In accordance with at least one embodiment of the disclosure, the oxyalkylenated nonionic surfactants are chosen from oxyethylenated $C_8$-$C_{30}$ alcohols and polyoxyethylenated esters of linear or branched, saturated or unsaturated $C_8$-$C_{30}$ acids, and of sorbitan.

In at least one embodiment, monoglycerolated or polyglycerolated nonionic surfactants are chosen from, monoglycerolated and polyglycerolated $C_8$-$C_{40}$ alcohols.

For example, the monoglycerolated or polyglycerolated $C_8$-$C_{40}$ alcohols correspond to the following formula:

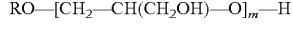

RO—[CH$_2$—CH(CH$_2$OH)—O]$_m$—H wherein R is chosen from a linear or branched $C_8$-$C_{40}$, for example a $C_8$-$C_{30}$ alkyl or alkenyl radical, and m is chosen from a number ranging from 1 to 30, for example a number ranging from 1 to 10.

As examples of compounds that may be used in the context of the present disclosure herein, non-limiting mention may be made of lauryl alcohol comprising 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol comprising 2 mol of glycerol, cetearyl alcohol comprising 6 mol of glycerol, oleocetyl alcohol comprising 6 mol of glycerol, and octadecanol comprising 6 mol of glycerol.

The alcohol may be chosen from a mixture of alcohols in the same way that the value of m may be chosen from a statistical value, so that two or more species of polyglycerolated fatty alcohol may coexist in the form of a mixture.

In at least one embodiment, the monoglycerolated or polyglycerolated alcohols, are chosen from the $C_8$/$C_{10}$ alcohol comprising 1 mol of glycerol, the $C_{10}$/$C_{12}$ alcohol comprising 1 mol of glycerol and the $C_{1-2}$ alcohol comprising 1.5 mol of glycerol.

The at least one surfactant comprised in composition (A) may be chosen from a nonionic surfactant and a mixture of nonionic surfactants.

The at least one surfactant content of composition (A) may be chosen from 0.1% to 50% by weight, for example from 0.5% to 30% by weight relative to the weight of the composition (A).

The at least one substantially anhydrous or aqueous composition (A) may optionally comprise at least one alkaline agents.

The at least one alkaline agent may be chosen from organic amines or salts thereof, mineral bases and ammonium salts, and mixtures thereof.

In at least one embodiment, the organic amines are chosen from organic amines whose pK$_b$ at 25° C. is less than 12, for example less than 10 further for example less than 6.

It should be noted that it is the pK$_b$ corresponding to the function of highest basicity.

In at least one embodiment, the organic amine(s) according to the present disclosure may not comprise a fatty chain comprising more than 10 carbon atoms.

According to another embodiment, the organic amines comprise one or two primary, secondary or tertiary amine functions, and at least one linear or branched $C_1$-$C_8$ alkyl groups bearing at least one hydroxyl radical.

The organic amines may be chosen from alkanolamines such as mono-, di- or trialkanolamines comprising one to three identical or different $C_1$-$C_4$ hydroxyalkyl radicals.

Among the organic amines, non-limiting mention may be made of, for example, monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

Also suitable for use, for example, are the organic amines having the following formula:

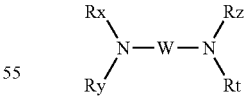

wherein W is a $C_1$-$C_6$ alkylene residue optionally substituted with a hydroxyl group or a $C_1$-$C_6$ alkyl radical; Rx, Ry, Rz and Rt, which may be identical or different, are chosen from a hydrogen atom, a $C_1$-$C_6$ alkyl, $C_1$-$C_6$ hydroxyalkyl and $C_1$-$C_6$ aminoalkyl radical.

Examples of such amines may include 1,3-diaminopropane, 1,3-diamino-2-propanol, spermine and spermidine.

The organic amine may also be chosen from amino acids.

For example, amino acids that may be used are, for example, of natural or synthetic origin, in their L, D or racemic form, and comprise at least one acid function for example chosen from carboxylic, sulfonic, phosphonic and phosphoric acid functions. The amino acids may be in neutral or ionic form.

As amino acids that may be used according to the present disclosure, non-limiting mention may be made, for example of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

According to at least one embodiment, the amino acids are basic amino acids comprising an additional amine function optionally included in a ring or in a ureido function.

Such basic amino acids are chosen from those corresponding to formula (II) below:

$$R-CH_2-CH\begin{matrix}NH_2\\CO_2H\end{matrix} \quad (II)$$

wherein R is chosen from:

[structures] —(CH$_2$)$_3$NH$_2$; —(CH$_2$)$_2$NH$_2$;
—(CH$_2$)$_2$NHCONH$_2$; and
—(CH$_2$)$_2$NH—C(=NH)—NH$_2$ The compounds corresponding to formula (II) comprise histidine, lysine, arginine, ornithine and citrulline.

According to at least one embodiment of the present disclosure, the amino acid is basic and chosen from, for example, arginine, lysine and histidine, and mixtures thereof.

The organic amine may also be chosen from organic amines of heterocyclic type. In addition to histidine, non-limiting mention may be made for example of pyridine, piperidine, imidazole, triazole, tetrazole and benzimidazole.

The organic amine may also be chosen from amino acid dipeptides. Amino acid dipeptides that may be used according to the present disclosure, include, for example, carnosine, anserine, and baleine.

The organic amine may also be chosen from compounds comprising a guanidine function. Amines of this type that may be used according to the present disclosure, in addition to arginine, include, for example, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)-methyl]amino)ethane-1-sulfonic acid.

Salts of the abovementioned amines may also be used, for instance organic or mineral salts of an organic amine as described below.

For example, the organic salts may be chosen from organic acid salts such as citrates, lactates, glycolates, gluconates, acetates, propionates, fumarates, oxalates and tartrates.

For example, mineral salts may be chosen from hydrohalides (for example hydrochlorides), carbonates, hydrogen carbonates, sulfates, hydrogen phosphates and phosphates.

Mineral base(s) may be chosen from those comprising in their structure at least one element from columns 1 to 13 of the Periodic Table of the Elements other than hydrogen, not simultaneously comprising carbon and hydrogen atoms. According to at least one embodiment of the present disclosure, the mineral base comprises at least one element from columns 1 and 2 of the Periodic Table of the Elements other than hydrogen.

In at least one embodiment, the mineral base comprises the following structure:

$$(Z_1^{x-})_m(Z_2^{y+})_n$$

wherein:

$Z_2$ is chosen from a metal from columns 1 to 13 for example, chosen from columns 1 and 2, of the Periodic Table of the Elements, for instance sodium or potassium;

$Z_1^{x-}$ is chosen from an anion chosen from the ions $CO_3^{2-}$, $OH^-$, $HCO_3^{2-}$, $SiO_3^{2-}$, $HPO_4^{2-}$, $PO_4^{3-}$ and $B_4O_7^{2}$, for example from the ions $CO_3^{2-}$, $OH^-$ and $SiO_3^{2-}$;

x is an integer chosen from 1, 2 and 3;

y is an integer chosen from 1, 2, 3 and 4;

m and n independently are integers chosen from 1, 2, 3 and 4; with n.y=m.x.

For example, the mineral base corresponds to the following formula $(Z_1^{x-})_m(Z_2^{y+})_n$, wherein $Z_2$ is chosen from a metal chosen from columns 1 and 2 of the Periodic Table of the Elements; $Z_1^{x-}$ is chosen from an anion chosen from the ions $CO_3^{2-}$, $OH^-$ and $SiO_3^{2-}$, x is 1, y is an integer chosen from 1 and 2, m and n are integers independently chosen from 1 and 2 with n.y=m.x.

Mineral bases that may be used according to the present disclosure include, for example, sodium carbonate, potassium carbonate, sodium hydroxide, potassium hydroxide, sodium metasilicate and potassium metasilicate. For example, the mineral base is an alkali metal carbonate.

The ammonium salts may be chosen from the following acid salts: acetate, carbonate, bicarbonate, chloride, citrate, nitrate, nitrite, phosphate, and sulfate.

In one embodiment of the present disclosure the ammonium salt is ammonium carbonate.

In one embodiment, at least one substantially anhydrous or aqueous composition (A) does not comprise any persalts.

In one embodiment, the alkaline agent is chosen from alkanolamines, basic amino acids, alkali metal hydroxides or carbonates. In another embodiment, the alkaline agent is chosen from alkanolamines optionally mixed with basic amino acids, and alkali metal hydroxides or carbonates.

According to at least one one embodiment of the present disclosure, the alkaline agent is monoethanolamine, used alone or as a mixture with the abovementioned alkaline agents; for example with a mineral base, for instance sodium hydroxide or potassium carbonate, and/or with a basic amino acid, for instance, such as arginine.

In one embodiment, if at least one substantially anhydrous or aqueous composition (A) comprises at least one alkaline agent, they are present in a content ranging from 0.01% to 30% by weight, for example from 0.1% to 20% by weight and further for example from 0.1% to 10% by weight relative to the weight of the said composition.

The at least one substantially anhydrous or aqueous composition (A) may further comprise various adjuvants which are used conventionally in the art, such as anionic, cationic, nonionic, amphoteric and zwitterionic polymers or mixtures thereof; mineral thickeners, for instance fillers such as clays, and talc; organic thickeners, for example with anionic, cationic, nonionic and amphoteric polymeric associative thickeners; mineral thickeners chosen from organophilic clays, fumed silicas; antioxidants; penetrants; sequestrants; fragrances; dispersants; film-forming agents; ceramides; preserving agents; opacifiers; and conditioning agents, for instance with cationic polymers.

The above adjuvants are generally present in an amount, for each of them, ranging from 0.01% to 20% by weight relative to the weight of at least one substantially anhydrous or aqueous composition (A).

The method according to the present disclosure is also carried out in the presence of at least one substantially anhydrous or aqueous composition (B) comprising at least one compounds of formula (I) above.

In the formula (I), $R_1$ and $R_2$ may be identical.

According to at least one embodiment, the compound of formula (I) comprises only one silicon atom.

Non-limiting examples of compounds of formula (I) may include the following compounds:

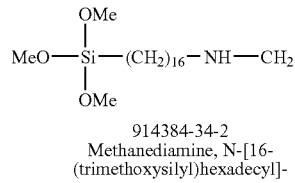

914384-34-2
Methanediamine, N-[16-(trimethoxysilyl)hexadecyl]-

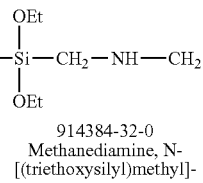

914384-32-0
Methanediamine, N-[(triethoxysilyl)methyl]-

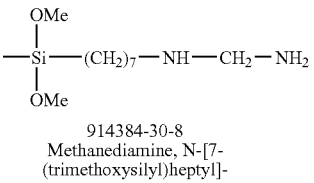

914384-30-8
Methanediamine, N-[7-(trimethoxysilyl)heptyl]-

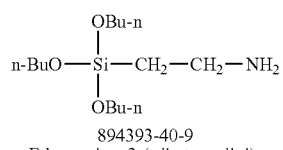

894393-40-9
Ethanamine, 2-(tributoxysilyl)-

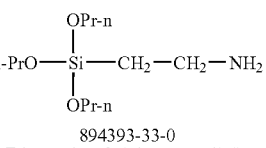

894393-33-0
Ethanamine, 2-(tripropoxysilyl)-

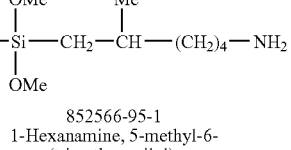

852566-95-1
1-Hexanamine, 5-methyl-6-(trimethoxysilyl)-

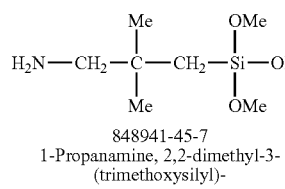

848941-45-7
1-Propanamine, 2,2-dimethyl-3-(trimethoxysilyl)-

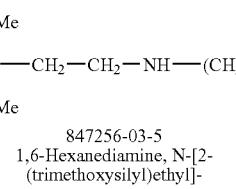

847256-03-5
1,6-Hexanediamine, N-[2-(trimethoxysilyl)ethyl]-

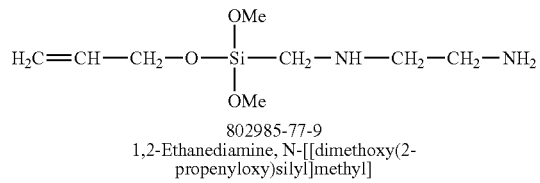

802985-77-9
1,2-Ethanediamine, N-[[dimethoxy(2-propenyloxy)silyl]methyl]

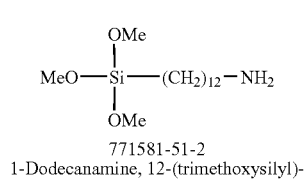

771581-51-2
1-Dodecanamine, 12-(trimethoxysilyl)-

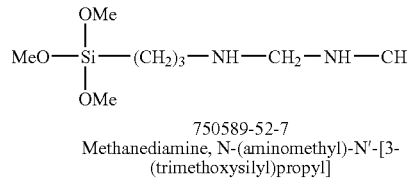

750589-52-7
Methanediamine, N-(aminomethyl)-N'-[3-(trimethoxysilyl)propyl]

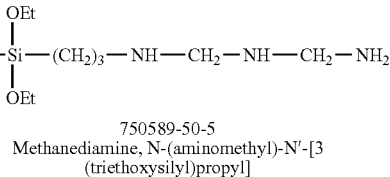

750589-50-5
Methanediamine, N-(aminomethyl)-N'-[3-(triethoxysilyl)propyl]

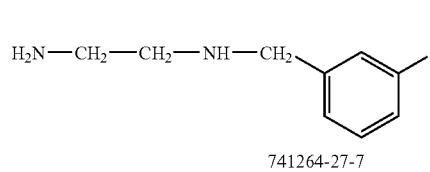

741264-27-7
1,2-Ethanediamine, N-[[3-[2-(trimethoxysilyl)ethyl]phenyl]methyl]-

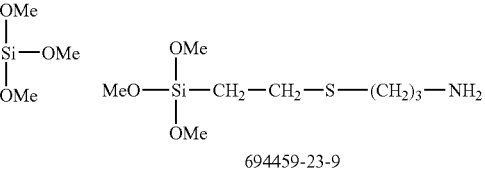

694459-23-9
1-Propanamine, 3-[[2-(trimethoxysilyl)ethyl]thio]-

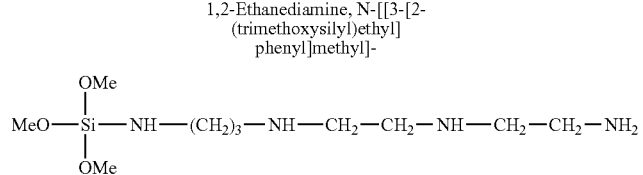

680220-31-9
1,3-Propanediamine, N-[2[(2-aminoethyl)amino]ethyl]-N'-(trimethoxysilyl)-

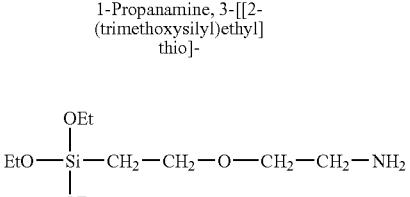

674778-27-9
Ethanamine, 2-[2-(triethoxysilyl)ethoxy]-

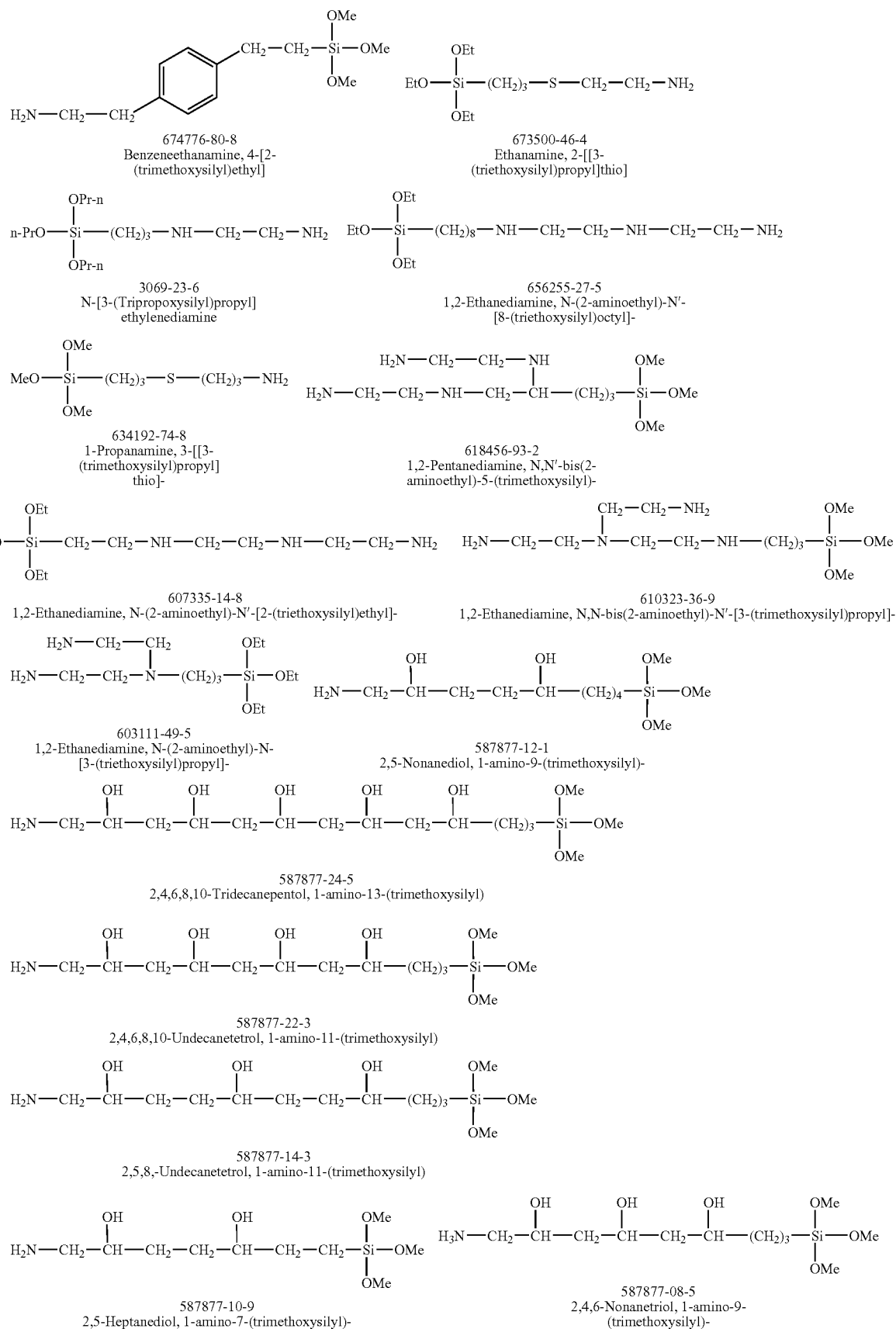

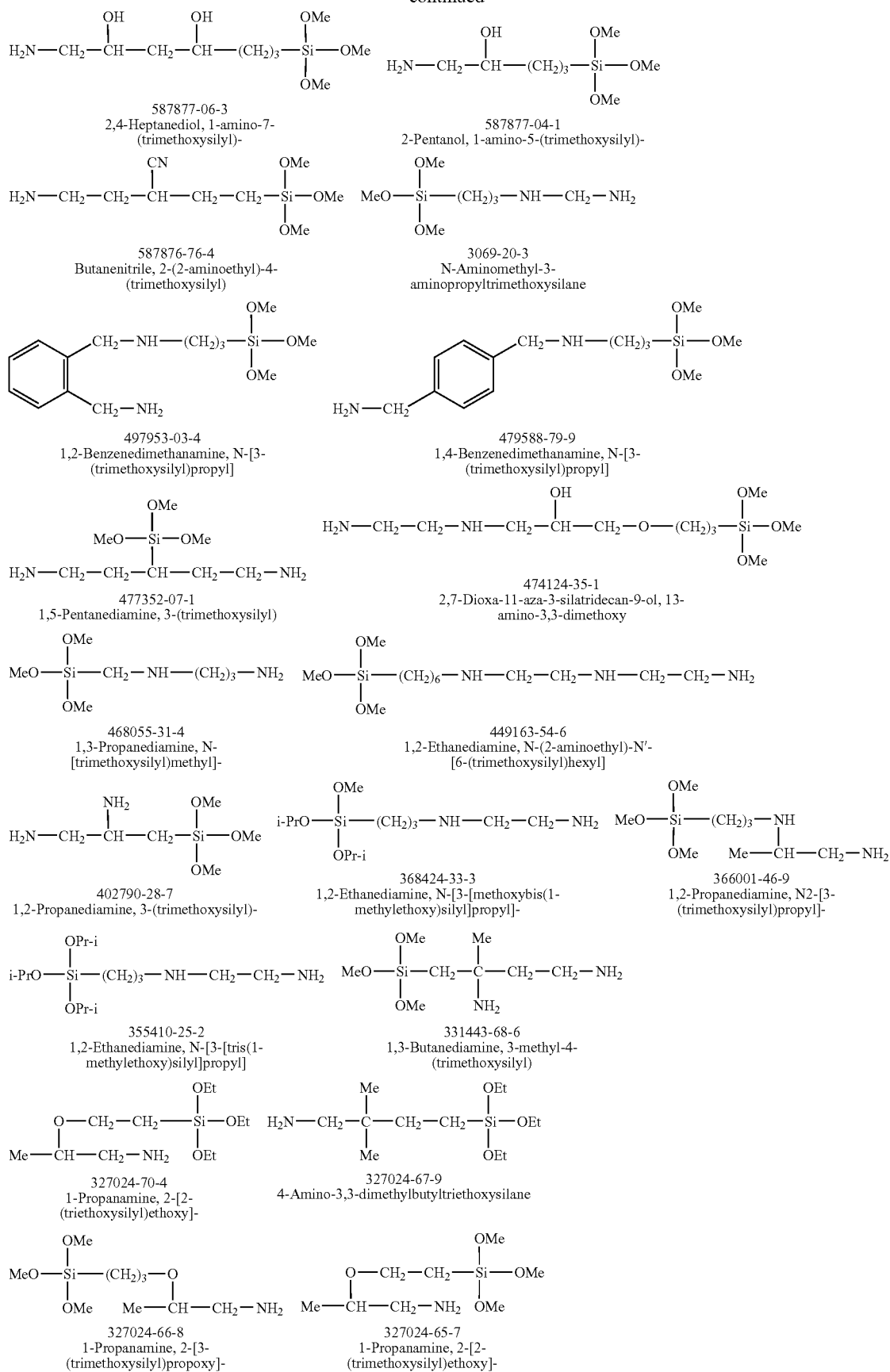

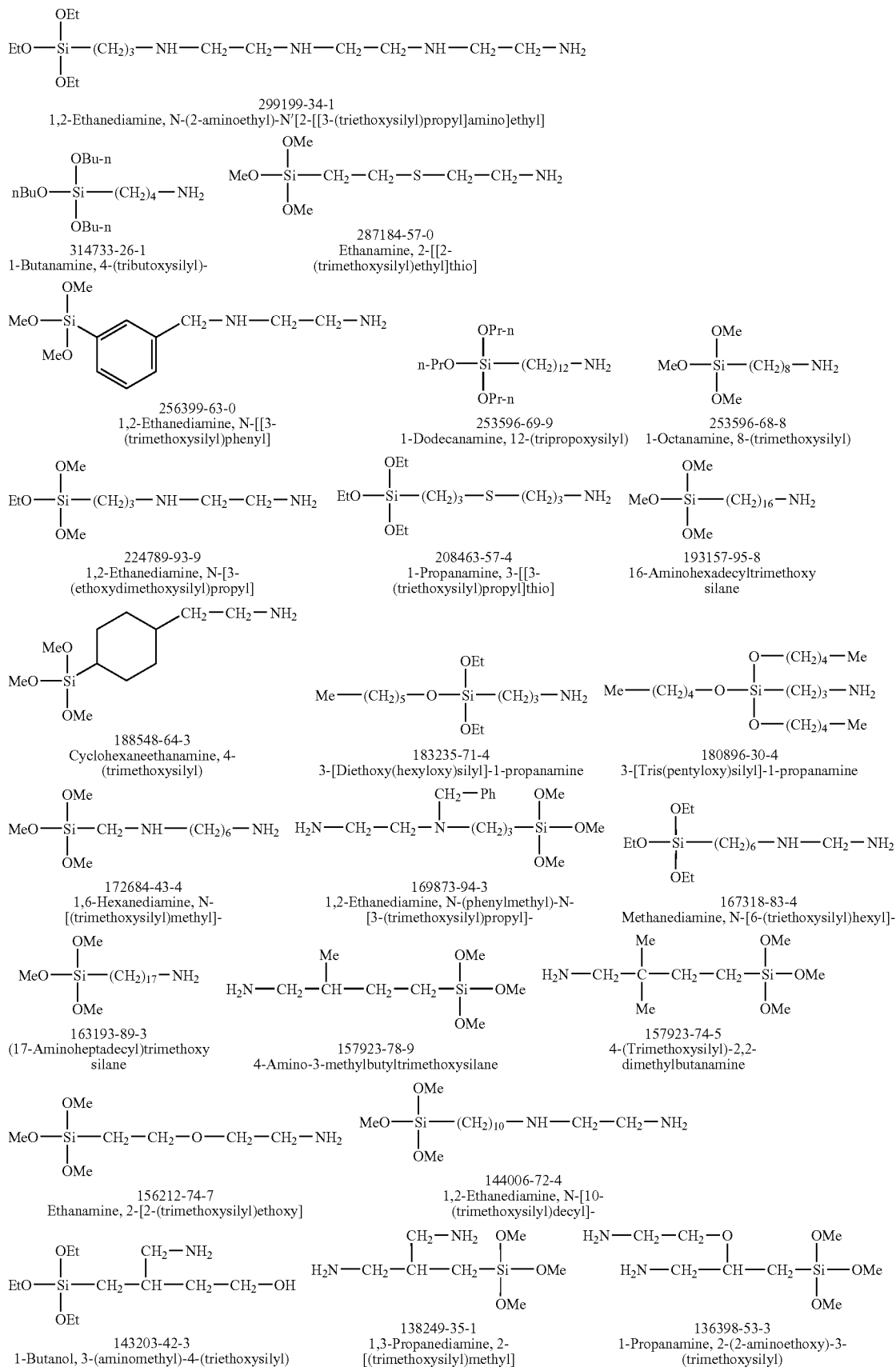

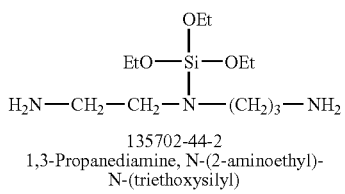

135702-44-2
1,3-Propanediamine, N-(2-aminoethyl)-N-(triethoxysilyl)

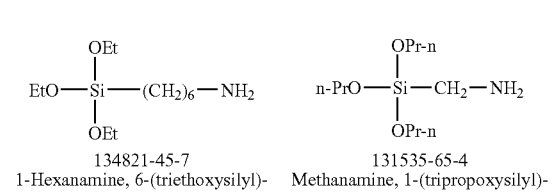

134821-45-7
1-Hexanamine, 6-(triethoxysilyl)-

131535-65-4
Methanamine, 1-(tripropoxysilyl)-

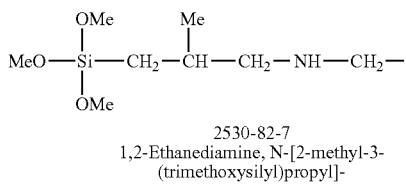

2530-82-7
1,2-Ethanediamine, N-[2-methyl-3-(trimethoxysilyl)propyl]-

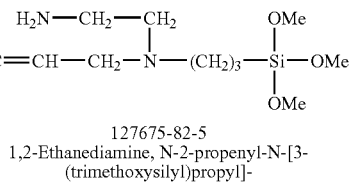

127675-82-5
1,2-Ethanediamine, N-2-propenyl-N-[3-(trimethoxysilyl)propyl]-

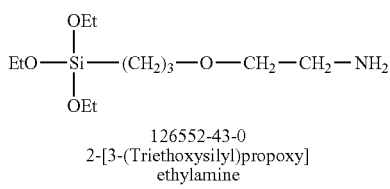

126552-43-0
2-[3-(Triethoxysilyl)propoxy]ethylamine

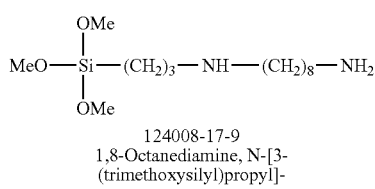

124008-17-9
1,8-Octanediamine, N-[3-(trimethoxysilyl)propyl]-

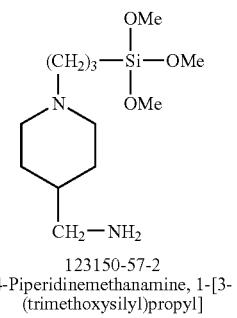

123150-57-2
4-Piperidinemethanamine, 1-[3-(trimethoxysilyl)propyl]

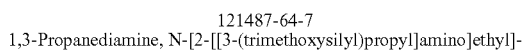

121487-64-7
1,3-Propanediamine, N-[2-[[3-(trimethoxysilyl)propyl]amino]ethyl]-

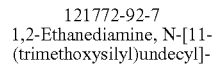

121772-92-7
1,2-Ethanediamine, N-[11-(trimethoxysilyl)undecyl]-

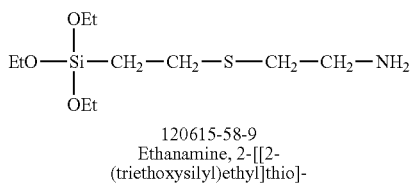

120615-58-9
Ethanamine, 2-[[2-(triethoxysilyl)ethyl]thio]-

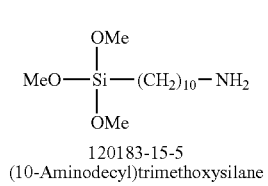

120183-15-5
(10-Aminodecyl)trimethoxysilane

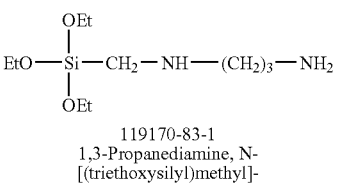

119170-83-1
1,3-Propanediamine, N-[(triethoxysilyl)methyl]-

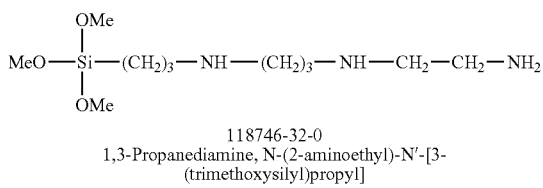

118746-32-0
1,3-Propanediamine, N-(2-aminoethyl)-N'-[3-(trimethoxysilyl)propyl]

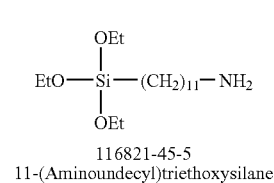

116821-45-5
11-(Aminoundecyl)triethoxysilane

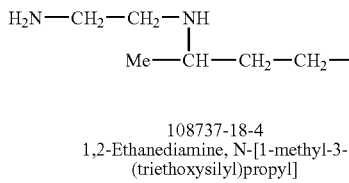

108737-18-4
1,2-Ethanediamine, N-[1-methyl-3-(triethoxysilyl)propyl]

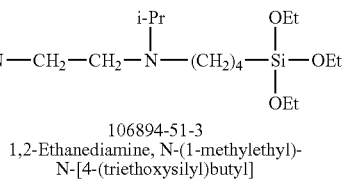

106894-51-3
1,2-Ethanediamine, N-(1-methylethyl)-N-[4-(triethoxysilyl)butyl]

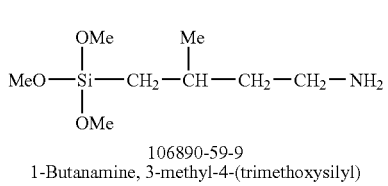

106890-59-9
1-Butanamine, 3-methyl-4-(trimethoxysilyl)

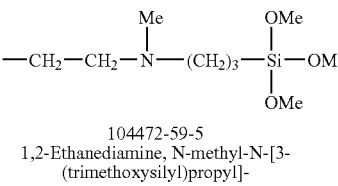

104472-59-5
1,2-Ethanediamine, N-methyl-N-[3-(trimethoxysilyl)propyl]-

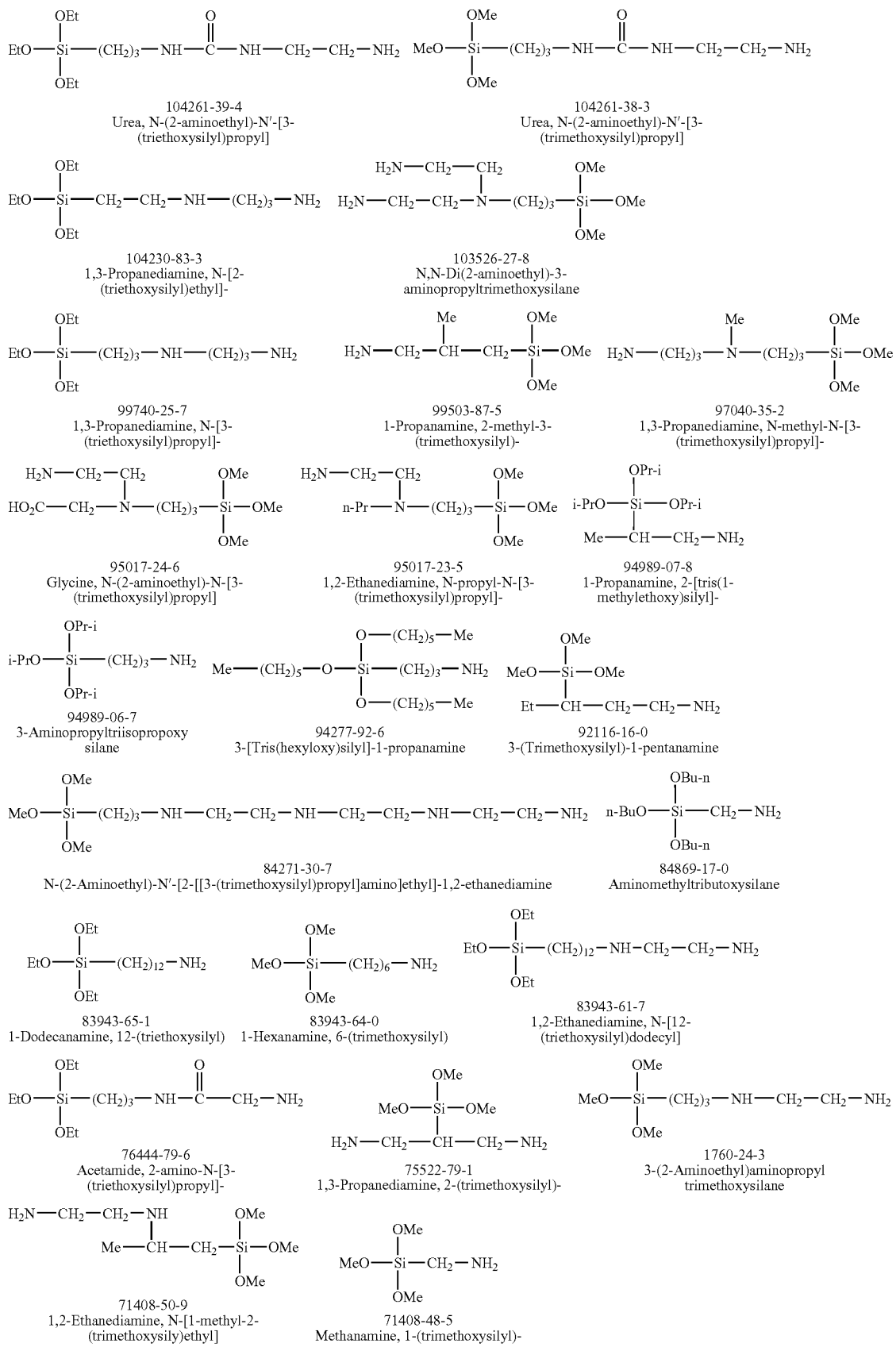

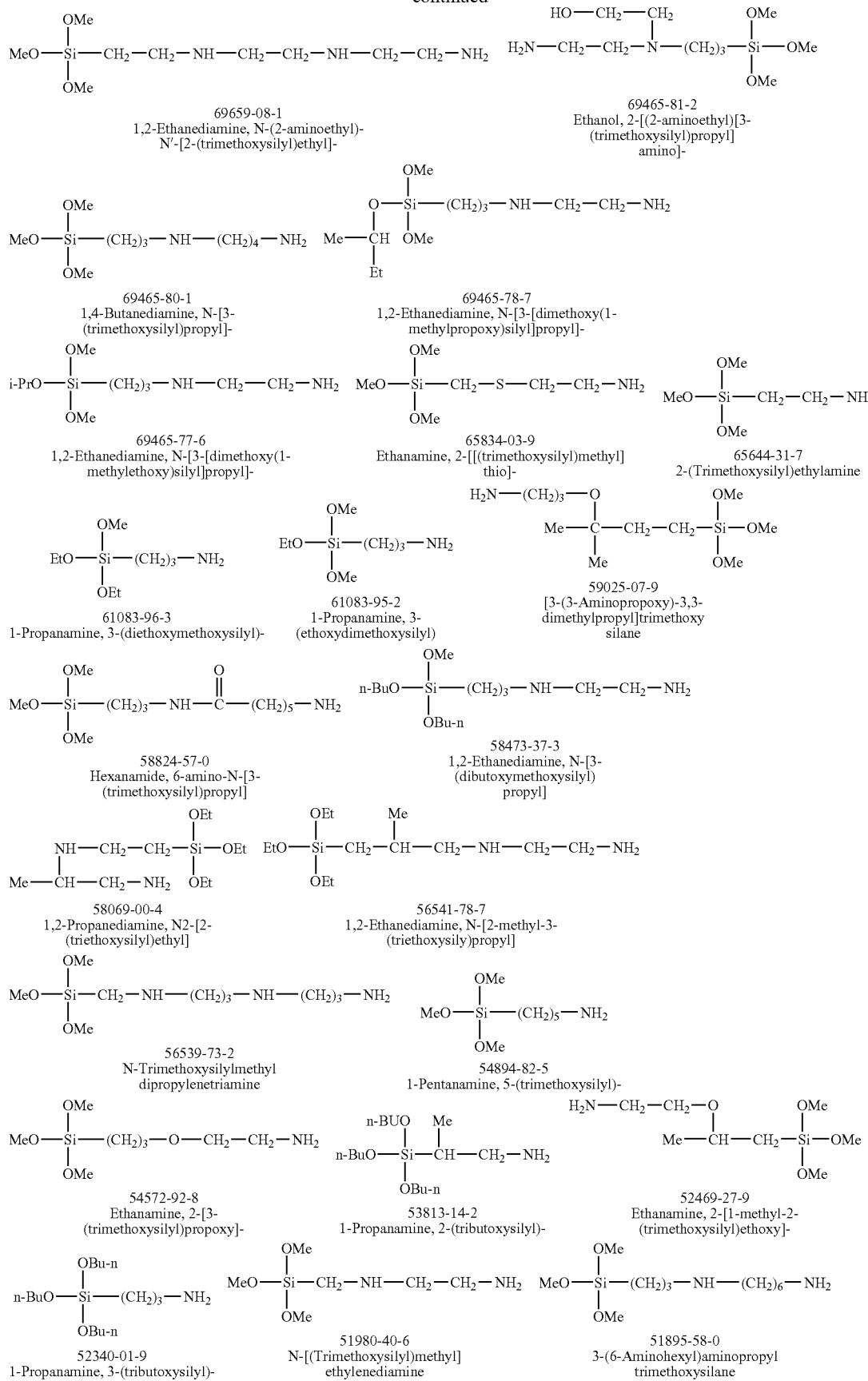

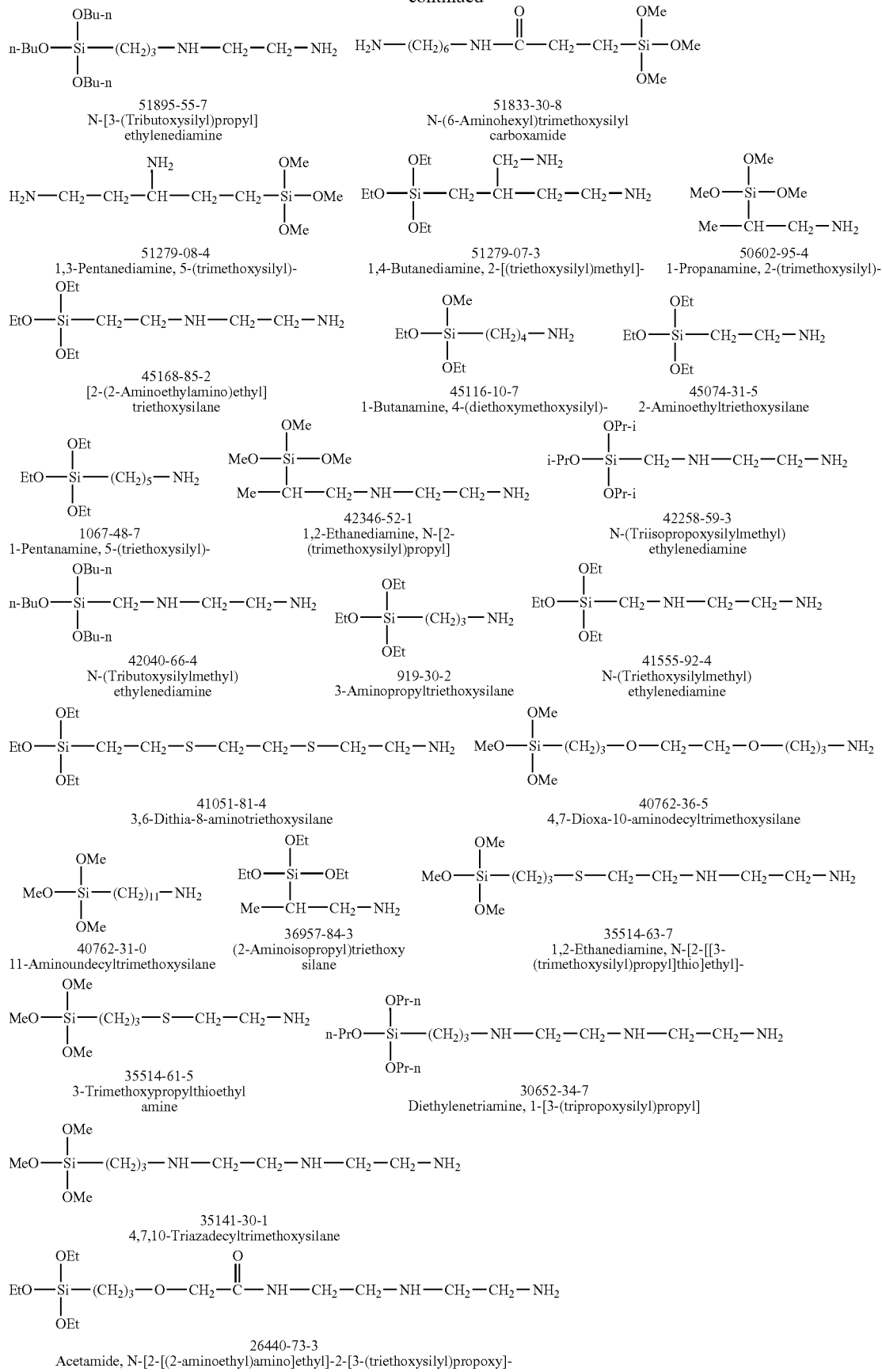

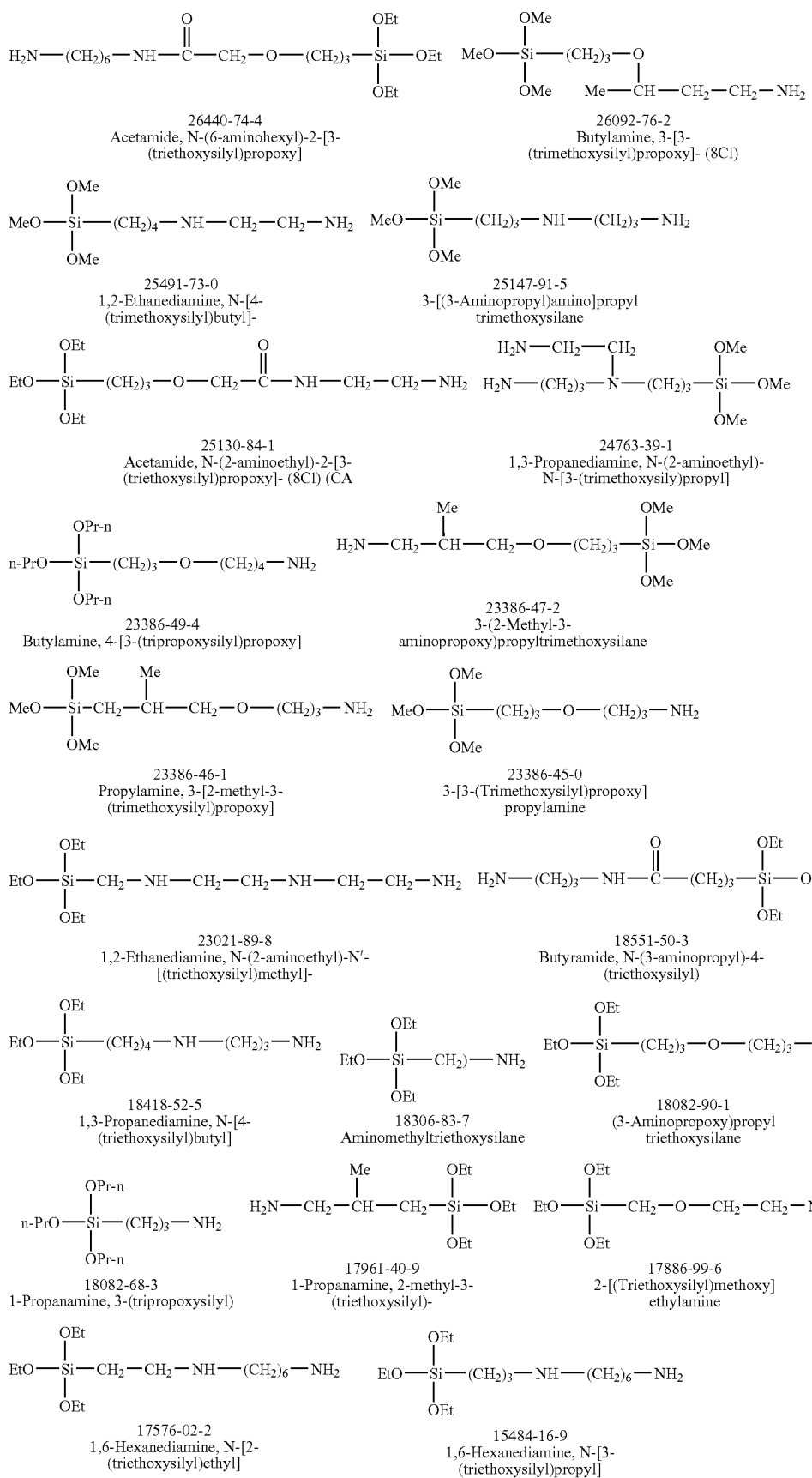

-continued

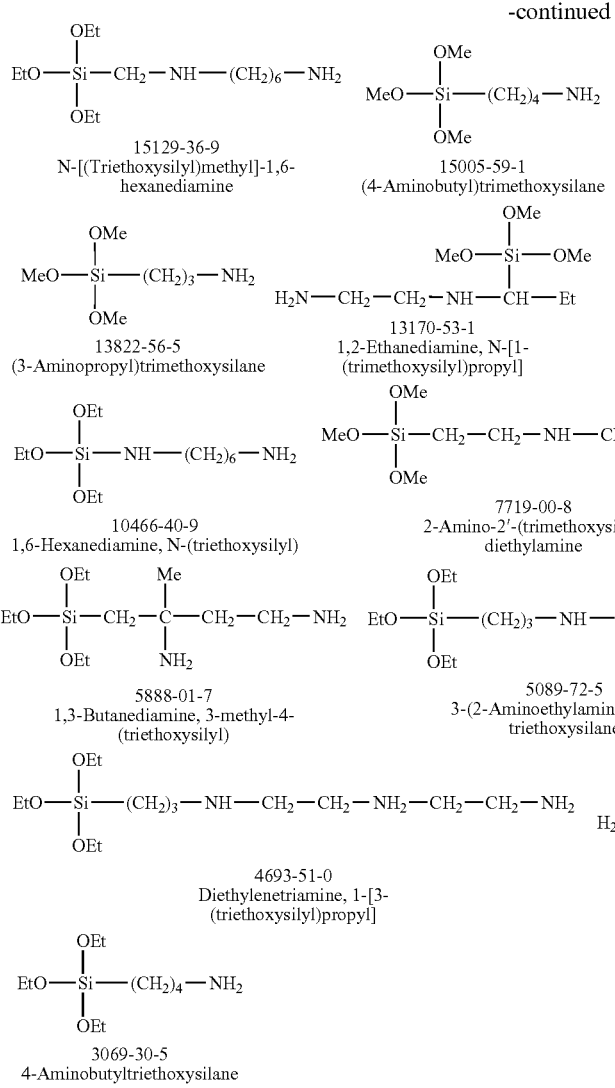

The compounds of formula (I) may comprise at least one silicon atom bearing three alkoxy or alkenyloxy groups.

In formula (I), $R_1$ and $R_2$ may be identical.

According to another embodiment, $R_1$, $R_2$ and $R_3$ are identical.

In accordance with at least one embodiment, the coefficients k, n and s are 0.

According to at least one embodiment, the compound of formula (I) comprises only one silicon atom.

According to another embodiment of the present disclosure, the compounds of formula (I) comprise only one silicon atom bearing three $C_1$-$C_4$ alkoxy groups.

According to this embodiment, $R_1$, $R_2$ and $R_3$ may be identical.

In accordance with at least one embodiment, the coefficients k, n and s are, for example 0; and p is 1.

In accordance with an additional embodiment, the compounds of formula (I) may be such that, the coefficients r, j and m are zero. In at least one embodiment, the compounds of formula (I) are comprised such that i is zero.

According to at least one embodiment of the invention, the compound of formula (I) is 3-aminopropyl)triethoxysilane.

In one embodiment, the amount of compounds of formula (I) ranges from 0.1% to 65% by weight relative to the total weight of composition (B).

The amount of compounds of formula (I) may range from 0.1% to 50%, for example from 1% to 30%, by weight relative to the weight of at least one substantially anhydrous or aqueous composition (B).

According to another embodiment of the present disclosure, the amount of compounds of formula (I) is chosen from 20% to 65%, for example from 30% to 60%, further for example from 40% to 50%, by weight relative to the weight of at least one substantially anhydrous or aqueous composition (B).

When at least one substantially anhydrous or aqueous composition (B) is aqueous, the at least one organosilicon compound may be partially neutralized with a neutralizer or pH regulator, such that the neutralization reaches 1/1000 to 99/100 for example from 0.2/100 to 70/100. Further for example, the neutralization is from 0.2/100 to 60/100.

The pH regulators may be any cosmetically acceptable acids or mixture of acids that are soluble in the medium of the composition. Among the acids that may be used, non-limiting mention may be made of, for example, hydrochloric acid, phosphoric acid, sulfonic acid and organic acids. The composition used according to the invention may also comprise at least one other organic acid.

The organic acids may generally be chosen from acids comprising at least one carboxylic, sulfonic, phosphonic or phosphoric acid functions. They may comprise other chemical functions, for example hydroxyl or amino functions. They may be saturated or unsaturated. Non-limiting mention may be made, for example of acetic acid, propanoic acid, butanoic acid, lactic acid, glycolic acid, ascorbic acid, maleic acid, phthalic acid, succinic acid, taurine, tartaric acid, gluconic acid, glucuronic acid and citric acid. Further for example, the organic acids are chosen from lactic acid, acetic acid and citric acid.

The composition comprising the at least one organosilicon compound may further comprise at least one thickener. The thickeners may be chosen from fatty acid amides (coconut diethanolamide or monoethanolamide, oxyethylenated alkyl ether carboxylic acid monoethanolamide), cellulose-based thickeners (hydroxyethylcellulose, hydroxypropylcellulose, carboxymethylcellulose), guar gum and derivatives thereof (hydroxypropyl guar), gums of microbial origin (xanthan gum, scleroglucan gum), and crosslinked acrylic acid or acrylamidopropanesulfonic acid homopolymers.

At least one substantially anhydrous or aqueous composition (A) and/or at least one substantially anhydrous or aqueous composition (B) may also comprise:

at least one oxidation dye precursor, for example, at least one oxidation base optionally combined with at least one coupler,
at least one synthetic direct dye,
at least one natural dye,
or mixtures thereof.

According to at least one one embodiment of the present disclosure, at least one substantially anhydrous or aqueous composition (A) may further comprise:

at least one oxidation dye precursor, for example at least one oxidation base optionally combined with at least one coupler,
at least one synthetic direct dye,
at least one natural dye,
or mixtures thereof.

According to at least one one embodiment of the present disclosure at least one substantially anhydrous or aqueous composition (B) may further comprise:

at least one oxidation dye precursor, for example at least one oxidation base optionally combined with at least one coupler,
at least one synthetic direct dye,
at least one natural dye,
or mixtures thereof.

By way of example, the at least one oxidation base is chosen from para-phenylenediamines, bis(phenyl)alkylenediamines, para-aminophenols, ortho-aminophenols and heterocyclic bases, and the addition salts thereof.

Among the para-phenylenediamines non-limiting mention may be made of, for example, para-phenylenediamine, para-tolylenediamine, 2-chloro-para-phenylenediamine, 2,3-dimethyl-para-phenylenediamine, 2,6-dimethyl-para-phenylene-diamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-p-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines, non-limiting mention may be made of, for example, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

Among the bis(phenyl)alkylenediamines non-limiting mention may be made of, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl) tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols non-limiting mention may be made of, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols non-limiting mention may be made of, for example, 2-aminophenol, 2-amino-5-methylphenol, 2-amino-6-methylphenol, and 5-acetamido-2-aminophenol, and the addition salts thereof.

Among the heterocyclic bases non-limiting mention may be made of, for example, pyridine derivatives, pyrimidine derivatives, and pyrazole derivatives.

Among the pyridine derivatives non-limiting mention may be made of, for example the compounds described, for example, in patents GB 1 026 978 and GB 1 153 196, for instance 2,5-diaminopyridine, 2-(4-methoxyphenyl)amino-3-amino-pyridine, and 3,4-diaminopyridine, and the addition salts thereof.

Other pyridine oxidation bases that may be useful in the compositions of the present disclosure are, for example the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)

ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives, non-limiting mention may be made of, for example, the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives non-limiting mention may be made of the compounds described, for example, in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methyl-pyrazole, 4,5-diamino-1-(β-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-diamino-1-(β-methoxyethyl)pyrazole may also be used.

Among pyrazole derivatives non-limiting mention may be made of, for example, diamino-N,N-dihydropyrazolopyrazolones and those described in patent application FR 2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Heterocyclic bases that may be used include, for example 4,5-diamino-1-(β-hydroxyethyl)pyrazole and/or 2,3-diamino-6,7-dihydro-1H,5H-pyrazolo[1,2-a]pyrazol-1-one and the addition salts thereof.

Examples of cationic oxidation bases that may be used include, for example the following compounds: para-phenylenediamines for instance, as described in patent applications FR-A-2 766 177 and FR-A-2 766 178, para-aminophenols as described, for example, in patent applications FR-A-2 766 177 and FR-A-2 766 178, ortho-phenylenediamines as described, for example, in patent applications FR-A-2 782 718, FR-A-2 782 716 and FR-A-2 782 719, ortho-aminophenols or cationic double bases such as derivatives of the bis (aminophenyl)alkylenediamine type described in patent application FR-A-2 766 179, and also cationic heterocyclic bases, these compounds bearing at least one quaternary nitrogen atom.

In at least one embodiment, the cationic oxidation bases are cationic para-phenylenediamines.

In at least one embodiment, cationic oxidation bases of para-phenylene diamine structure are used, at least one of the amine functions of which is a tertiary amine bearing a pyrrolidine nucleus, the molecule comprising at least one quaternized nitrogen atom. Such bases are described, for example, in document EP-A-1 348 695.

The compositions according to the present disclosure may optionally comprise at least one coupler chosen from those conventionally used for the dyeing of keratin fibers.

Among the at least one coupler, non-limiting mention may be made of, for example, meta-phenylenediamines, meta-aminophenols, meta-diphenols, naphthalenic couplers and heterocyclic couplers, and also the addition salts thereof.

Non-limiting mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl-indole, 2-amino-3-hydroxypyridine, 6-hydroxybenzomorpholine, 3,5-diamino-2,6-dimethoxypyridine, 1-N-β-hydroxyethylpyamino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the at least one oxidation base and at least one coupler that may be used in the context of the present disclosure may be chosen from the addition salts with an acid such as the hydrochlorides, hydrobromides, sulfates, citrates, succinates, tartrates, lactates, tosylates, benzenesulfonates, phosphates and acetates.

The at least one oxidation base, when present in the composition, may range, for example from 0.0001% to 10% by weight relative to the weight of the composition, for example from 0.005% to 5% by weight relative to the weight of the composition.

The at least one coupler, if they are present, may range, for example from 0.0001% to 10% by weight relative to the weight of the composition, for example from 0.005% to 5% by weight relative to the weight of the composition.

Non-limiting examples of at least one synthetic direct dye that may be used in the context of the present disclosure include, for example, the following direct dyes: azo dyes; methine dyes; carbonyl dyes; azine dyes; nitro (hetero)aryl dyes; tri(hetero)arylmethane dyes; alone or as mixtures.

For example, the azo dyes may comprise an —N═N— function where the two nitrogen atoms are not simultaneously engaged in a ring. However, it is not excluded for one of the two nitrogen atoms of the sequence —N═N— to be engaged in a ring.

The dyes of the methine family comprise compounds comprising at least one sequence selected from >C═C< and —N═C< wherein the two atoms are not simultaneously engaged in a ring. However, it is pointed out that one of the nitrogen or carbon atoms of the sequences may be engaged in a ring. For example, the dyes of this family are derived from compounds of true methine type (comprising at least one abovementioned sequence —C═C—); of azomethine type (comprising at least one, or more, sequences —C═N—) with, for example, azacarbocyanines and their isomers, diazacarbocyanines and their isomers, and tetraazacarbocyanines; of mono- and diarylmethane type; of indoamine (or diphenylamine) type; of indophenol type; or of indoaniline type.

With regard to the dyes of the carbonyl family, non-limiting mention may be made of, for example dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso) violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes.

With regard to the dyes of the azine family, non-limiting mention may be made of, for example, azine, xanthene, thioxanthene, fluorindine, acridine, (di)oxazine, (di)thiazine and pyronin dyes.

The nitro (hetero)aromatic dyes may be chosen from, for example, nitrobenzene and nitropyridine direct dyes.

With regard to the dyes of porphyrin or phthalocyanine type, it is possible to use cationic or non-cationic compounds, optionally comprising at least one metal or metal ions, for instance alkali metals, alkaline-earth metals, zinc and silicon.

Non-limiting examples of at least one synthetic direct dye include, for example, nitro dyes of the benzene series; azo direct dyes; methine direct dyes; azomethine direct dyes, diazacarbocyanines and isomers thereof and tetraazacarbocyanines (tetraazapentamethines); quinone direct dyes, and in particular anthraquinone, naphthoquinone or benzoquinone dyes; azine direct dyes; xanthene direct dyes; triarylmethane direct dyes; indoamine direct dyes; indigoid direct dyes; phthalocyanine and porphyrin direct dyes; alone or in mixtures.

The direct dyes may be chosen from nitro dyes of the benzene series; azo dyes; azomethine dyes, with the diazacarbocyanines and their isomers, the tetraazacarbocyanines (tetraazapentamethines); anthraquinone direct dyes; triarylmethane direct dyes; alone or in mixtures.

For example, direct dyes may be chosen from nitro dyes of the benzene series; azo direct dyes; azomethine direct dyes, with diazacarbocyanines and their isomers, and tetraazacarbocyanines (tetraazapentamethines); alone or in a mixture.

These dyes may be monochromophoric dyes (i.e. comprising only one dye) or polychromophoric, for example di- or trichromophoric, dyes; the chromophores may be identical or different, and from the same chemical family or otherwise. It should be noted that a polychromophoric dye comprises two or more radicals each derived from a molecule that absorbs in the visible region between 400 and 800 nm. Furthermore, this absorbance of the dye does not require any prior oxidation thereof, or combination with any other chemical species.

In the case of polychromophoric dyes, the chromophores are connected together by means of at least one linker, which may be cationic or non-cationic.

Among the nitrobenzenic direct dyes that may be used according to the present disclosure, mention may be made in a non-limiting manner of, for example, the following compounds: 1,4-diamino-2-nitrobenzene; 1-amino-2-nitro-4-β-hydroxy-ethylaminobenzene; 1-amino-2-nitro-4-bis(β-hydroxyethyl)aminobenzene; 1,4-bis(β-hydroxyethylamino)-2-nitrobenzene; 1-β-hydroxyethylamino-2-nitro-4-bis(β-hydroxyethyl-amino)benzene; 1-β-hydroxyethylamino-2-nitro-4-aminobenzene; 1-β-hydroxyethylamino-2-nitro-4-(ethyl)(β-hydroxyethyl)aminobenzene; 1-amino-3-methyl-4-β-hydroxyethylamino-6-nitrobenzene; 1-amino-2-nitro-4-β-hydroxyethylamino-5-chlorobenzene; 1,2-diamino-4-nitrobenzene; 1-amino-2-β-hydroxyethylamino-5-nitrobenzene; 1,2-bis(β-hydroxyethylamino)-4-nitrobenzene; 1-amino-2-tris(hydroxymethyl)methylamino-5-nitro-benzene; 1-hydroxy-2-amino-5-nitrobenzene, 1-hydroxy-2-amino-4-nitrobenzene; 1-hydroxy-3-nitro-4-aminobenzene; 1-hydroxy-2-amino-4,6-dinitrobenzene; 1-β-hydroxy-ethyloxy-2-β-hydroxyethylamino-5-nitrobenzene, 1-methoxy-2-β-hydroxyethylamino-5-nitrobenzene; 1-β-hydroxyethyloxy-3-methylamino-4-nitrobenzene; 1-β, γ-dihydroxypropyloxy-3-methylamino-4-nitrobenzene; 1-β-hydroxyethylamino-4-β,γ-dihydroxypropyloxy-2-nitrobenzene; 1-β,γ-dihydroxypropylamino-4-trifluoromethyl-2-nitrobenzene; 1β-hydroxyethylamino-4-trifluoromethyl-2-nitrobenzene; 1-β-hydroxyethylamino-3-methyl-2-nitrobenzene; 1-β-aminoethylamino-5-methoxy-2-nitrobenzene; 1-hydroxy-2-chloro-6-ethylamino-4-nitrobenzene; 1-hydroxy-2-chloro-6-amino-4-nitrobenzene; 1-hydroxy-6-bis(β-hydroxyethyl)amino-3-nitrobenzene; 1-β-hydroxy-ethylamino-2-nitrobenzene; 1-hydroxy-4-β-hydroxyethylamino-3-nitrobenzene.

Among the monochromophoric azo, azomethine, and methine direct dyes that may be used according to the present disclosure, non-limiting mention may be made, for example of the cationic dyes described in patent applications WO 95/15144, WO 95/01772 and EP 714 954; FR 2 189 006, FR 2 285 851, FR 2 140 205, EP 1 378 544 and EP 1 674 073.

Hence non-limiting mention may be made of, for example, the cationic direct dyes corresponding to the following formulae:

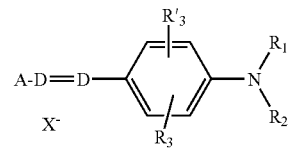

wherein:

D is chosen from a nitrogen atom and the —CH group, $R_1$ and $R_2$, which are identical or different, are chosen from a hydrogen atom; a $C_1$-$C_4$ alkyl radical which may be substituted with a —CN, —OH or —NH$_2$ radical, or form, with a carbon atom of the benzene ring, an optionally oxygen-comprising or nitrogen-comprising heterocycle which may be substituted with at least one $C_1$-$C_4$ alkyl radical; and a 4'-aminophenyl radical, $R_3$ and $R'_3$, which are identical or different, are chosen from a hydrogen or halogen atom selected from chlorine, bromine, iodine and fluorine, or a cyano, $C_1$-$C_4$ alkyl, $C_1$-$C_4$ alkoxy or acetyloxy radical, $X^-$ is an anion, for example an anion selected from chloride, methyl sulfate and acetate, A is chosen from a group selected from the following structures:

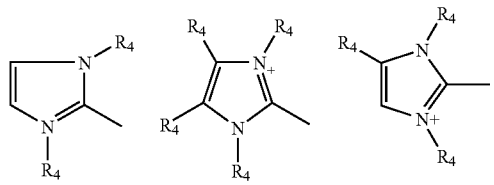

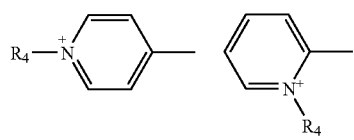

wherein $R_4$ is chosen from a $C_1$-$C_4$ alkyl radical which may be substituted with a hydroxyl radical;

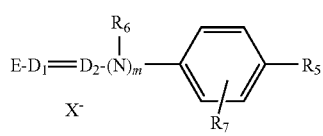

wherein:

$R_5$ is chosen from a hydrogen atom, a $C_1$-$C_4$ alkoxy radical and a halogen atom such as bromine, chlorine, iodine or fluorine, $R_6$ is chosen from a hydrogen atom, a $C_1$-$C_4$ alkyl radical, and a heterocycle formed with a carbon atom of the benzene ring and optionally oxygen-containing and/or substituted with at least one $C_1$-$C_4$ alkyl group, $R_7$ is chosen from a hydrogen and halogen atom such as bromine, chlorine, iodine or fluorine, $D_1$ and $D_2$, which are identical or different, are chosen from a nitrogen atom and the —CH group, m is an integer chosen from 0 and 1, $X^-$ is chosen from a cosmetically acceptable anion chosen from chloride, methyl sulfate and acetate, E is chosen from a group selected from the following structures:

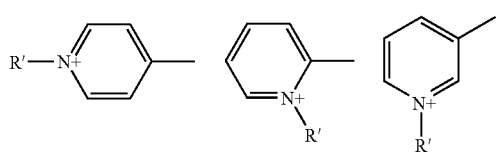

wherein R' is chosen from a $C_1$-$C_4$ alkyl radical; when m is 0 and when $D_1$ is a nitrogen atom, E may then also denote a group of the following structure:

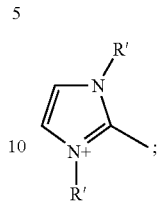

wherein R' is a $C_1$-$C_4$ alkyl radical.

Among the aforementioned compounds, use is made for example, of the following compounds:

(A1)
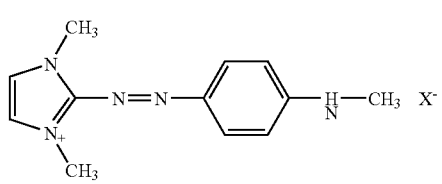

(A2)
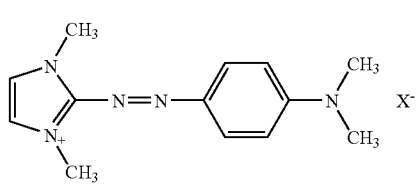

(A3)
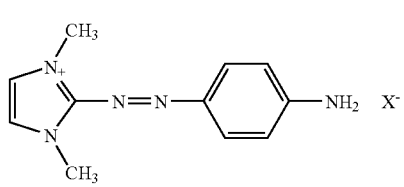

(A4)
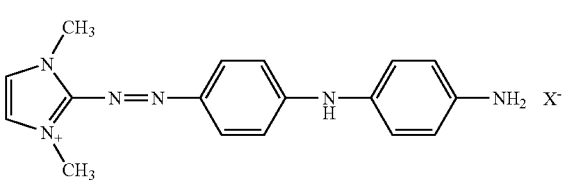

(A5)
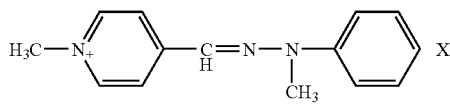

(A6)
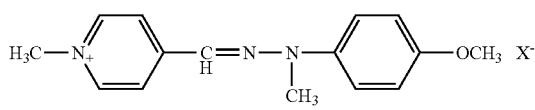

The tetraazapentamethine dyes that can be used according to the disclosure include, for example, the following compounds appearing in the table below:

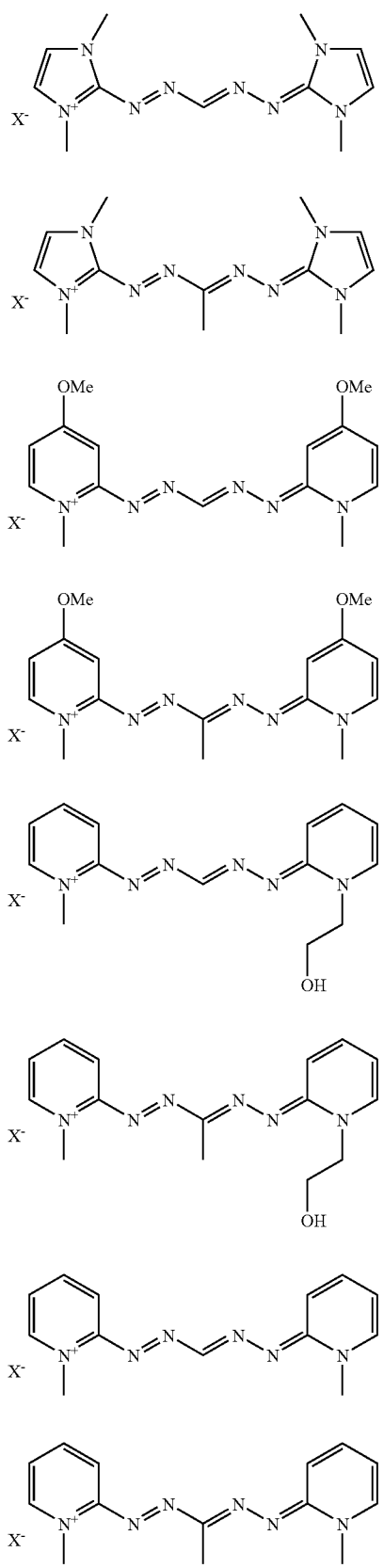

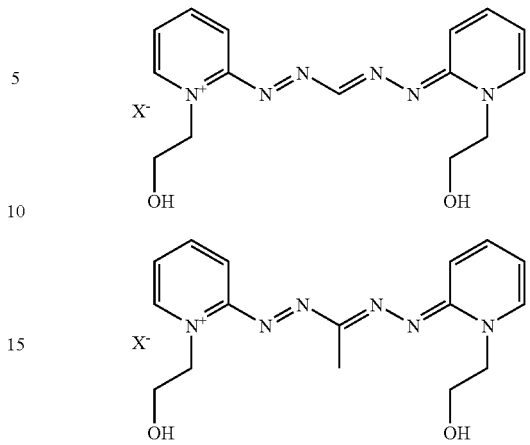

X⁻ is chosen from an anion chosen from chloride, iodide, methyl sulfate, ethyl sulfate and acetate.

Other dyes which can be used according to the present disclosure further include, among the azo direct dyes, the following dyes, which are described in the Colour Index International, 3rd edition: Disperse Red 17; Disperse Red 13; Basic Red 22; Basic Red 76; Basic Yellow 57; Basic Brown 16; Basic Brown 17; Disperse Green 9; Disperse Black 9; Solvent Black 3; Disperse Blue 148; Disperse Violet 63; Solvent Orange 7; 1-(4'-aminodiphenylazo)-2-methyl-4-bis (β-hydroxyethyl)aminobenzene (INCI name:HC Yellow 7).

Among the quinone direct dyes non-limiting mention may be made of, for example, the following dyes: Disperse Red 15; Solvent Violet 13; Solvent Blue 14; Disperse Violet 1; Disperse Violet 4; Disperse Blue 1; Disperse Violet 8; Disperse Blue 3; Disperse Red 11; Disperse Blue 7; Disperse Blue 14; Basic Blue 22; Disperse Violet 15; Disperse Blue 377; Disperse Blue 60; Basic Blue 99. It is also possible to mention the following compounds: 1-N-methylmorpholiniumpropylamino-4-hydroxyanthraquinone; 1-aminopropylamino-4-methylaminoanthraquinone; 1-aminopropylaminoanthraquinone; 5-β-hydroxyethyl-1,4-diaminoanthraquinone; 2-aminoethylaminoanthraquinone; 1,4-bis(βγ-dihydroxypropylamino)anthraquinone, and also the coumarin compound Disperse Yellow 82.

Among the azine dyes non-limiting mention may be made of, for example, the following compounds: Basic Blue 17; Basic Red 2; and Solvent Orange 15.

Among the triarylmethane dyes that may be used according to the present disclosure, non-limiting mention may be made of, for example, the following compounds: Basic Green 1; Basic Violet 3; Basic Violet 14; Basic Blue 7; and Basic Blue 26.

Among the indoamine dyes that may be used according to the present disclosure, non-limiting mention may be made of, for example, the following compounds: 2-β-hydroxyethylamino-5-[bis(β-4'-hydroxyethyl)amino]anilino-1,4-benzoquinone; 2-β-hydroxyethylamino-5-(2'-methoxy-4'-amino) anilino-1,4-benzoquinone; 3-N(2'-chloro-4'-hydroxy) phenylacetylamino-6-methoxy-1,4-benzoquinone imine; -3-N(3'-chloro-4'-methylamino)phenylureido-6-methyl-1,4-benzoquinone imine; and 3-[4'-N-(ethylcarbamylmethyl) amino]phenylureido-6-methyl-1,4-benzoquinone imine.

The cationic direct dyes may be chosen from monochromophoric direct dyes, for example, including: azo dyes, true methines; azomethines, with diaza-carbocyanines and their isomers, and tetraazacarbocyanines (tetraazapentamethines); anthraquinones; alone or in a mixture.

If direct dyes are present in at least one substantially anhydrous or aqueous composition (A) and/or (B), the content of direct dye(s) ranges from 0.005% to 20%, for example from 0.01% to 10% and further for example from 0.05% to 5% by weight relative to the weight of the said composition.

At least one substantially anhydrous or aqueous composition (A) and/or (B) may also comprise at least one natural dye chosen from lawsone, juglone, alizarin, purpurin, carminic acid, kermesic acid, purpurogallin, isatin, indigo, protocatechaldehyde, anthocyans, anthocyanidins, curcumin, orceins and apigenidin. The at least one natural dye may be used in their native form or from extracts.

If the at least one natural dye is present in at least one substantially anhydrous or aqueous composition (A) and/or (B), the content of the at least one natural dye ranges from 0.005% to 20%, for example ranging from 0.01% to 10% and further for example from 0.05% to 5% by weight relative to the weight of the said composition.

At least one substantially anhydrous or aqueous composition (B) may further comprise an alkaline agent other than the compounds of formula (I), which may be chosen from aqueous ammonia and from those described in the context of the at least one substantially anhydrous or aqueous composition (A).

For example, the alkaline agent is chosen from alkanolamines, basic amino acids and alkali metal hydroxides and carbonates.

Further for example, the alkaline agent is chosen from alkanolamines optionally as a mixture with basic amino acids or alkali metal hydroxides or carbonates.

According to at least one embodiment of the present disclosure, the alkaline agent is monoethanolamine, used alone or as a mixture with the abovementioned alkaline agents, for example with a mineral base, for instance sodium hydroxide or potassium carbonate, and/or alternatively with a basic amino acid such as, for example, arginine.

At least one substantially anhydrous or aqueous composition (B) may comprise a content of alkaline agent(s), if they are present, ranging from 0.1% to 30% by weight, for example ranging from 0.5% to 25% and further for example ranging from 1% to 20% by weight relative to the weight of the said composition.

The alkaline agent, and the pH regulators defined previously, may make it possible to adjust the pH of the composition applied to the hair.

According to at least one embodiment of the present disclosure, the pH of the composition applied to the hair ranges from 4 to 11 and for example ranges from 7 and 10.5.

According to another embodiment of the invention, the pH of the ready-to-use composition ranges from approximately 3 to approximately 12 for example, ranging from approximately 5 to approximately 11.

The composition comprising the at least one organosilicon compound generally has a pH ranging from 2 to 13, for example ranging from 4 to 11. For example, the pH of the composition obtained with a pH regulator ranges from 7 to 10.5 further for example, the pH ranges from 8 to 10.

If aqueous ammonia is used as an additional alkaline agent, then, in at least one embodiment, its content is less than or equal to 0.03% by weight of the final composition (expressed as NH$_3$), for example less than or equal to 0.01% by weight relative to the final composition. It is recalled that the final composition results from the mixing of the three compositions (A), (B) and (C); in at least one embodiment, this mixing being performed before application to the keratin fibers (extemporaneous preparation).

In at least one embodiment, at least one substantially anhydrous or aqueous composition (B) does not comprise any aqueous ammonia.

At least one substantially anhydrous or aqueous composition (B) may also comprise various adjuvants conventionally used in compositions for coloring the hair, such as anionic, cationic, nonionic, amphoteric or zwitterionic polymers or mixtures thereof; mineral thickeners, for example fillers such as clays or talc; organic thickeners, for instance with anionic, cationic, nonionic and amphoteric polymeric associative thickeners; antioxidants; penetrants; sequestrants; fragrances; dispersants; film-forming agents; ceramides; preservatives; opacifiers; conditioning agents, for example with cationic polymers.

The above adjuvants may generally be present in an amount, for each of them, ranging from 0.01% to 20% by weight relative to the weight of the composition.

Lastly, at least one aqueous composition (C) employed in the method according to the disclosure herein comprises at least one oxidizing agent, also known as anoxidizing composition.

In at least one embodiment, the at least one oxidixing agent is an oil-in-water direct emulsion.

In another embodiment, the at least one oxidizing agent is aqueous and optionally comprises at least one organic solvent.

The at least one organic solvent maybe chosen from, for example, linear or branched $C_2$-$C_4$ alkanols, such as ethanol and isopropanol; glycerol; glycols and glycol ethers, for instance 2-butoxyethanol, propylene glycol, dipropylene glycol, propylene glycol monomethyl ether, diethylene glycol monoethyl ether and monomethyl ether, and aromatic alcohols such as benzyl alcohol or phenoxyethanol, and mixtures thereof.

The at least one organic solvent may be present in proportions ranging from 1% to 40% by weight relative to the weight of the at least one oxidizing agent, for example from 5% to 30% by weight.

The at least one oxidizing agent may be chosen from hydrogen peroxide; urea peroxide; alkali metal ferricyanides or bromides; peroxygenated salts such as, for example, persulfates, perborates and percarbonates of alkali metals or alkaline earth metals, such as sodium, potassium and magnesium; or mixtures thereof. At least one redox enzyme(s) such as laccases, peroxidases and 2-electron oxidoreductases (such as uricase), optionally in the presence of the respective donor or cofactor thereof, may also be used as the at least one oxidizing agent.

The at least one oxidizing agent may be comprised of hydrogen peroxide, for example an aqueous solution whose titre may vary, for example from 1 to 40 volumes, and further for example from 5 to 40 volumes.

The at least one oxidizing agent may further comprise at least one basifying agent and/or at least one acidifying agent. For example, in one embodiment the at least one oxidizing agent comprises at least one acidifying agent.

Examples of the at least one acidifying agent include, for example, organic or inorganic acids, such as hydrochloric acid, orthophosphoric acid, sulfuric acid, carboxylic acids such as acetic acid, tartaric acid, citric acid and lactic acid, and sulfonic acids.

The pH of the at least one oxidizing agent is in at least one embodiment, less than 7, for instance, if the oxidizing agent is hydrogen peroxide.

The at least one oxidizing agent may take the form of a solution, an emulsion or a gel.

The amount of water in the at least one one aqueous composition (C) may range from 5% to 95% by weight, for example from 25% to 92% by weight, further for example from 40% to 90% by weight, relative to the weight of the composition (C).

The amount of water in at least one aqueous composition (C) may range from 10% and 90% by weight, relative to the weight of the emulsion.

When at least one aqueous composition (C) is an oil-in-water emulsion, it may comprise at least one fat as described in the context of at least one substantially anhydrous or aqueous composition (A).

When at least one aqueous composition (C) is an oil-in-water emulsion it may comprise at least 10% of fat. The fat concentration may range from 10% to 80%, for example from 15% to 65%, further for example from 20% to 55% of the total weight of the emulsion.

According to at least one embodiment, the at least one aqueous composition (C) as an oil-in-water emulsion comprises at least one oil. Examples include liquid petrolatum, liquid paraffin, polydecenes, and liquid fatty alcohol or fatty acid esters.

The at least one aqueous composition (C) as an oil-in-water emulsion may further comprise at least one surfactant.

The at least one surfactant may be chosen from nonionic surfactants and anionic surfactants.

The at least one surfactant present in the at least one aqueous composition (C) as an oil-in-water emulsion may comprise, for example an ethoxylated nonionic surfactant having an HLB of 8 to 18. The HLB is the ratio between the hydrophilic moiety and the lipophilic moiety in the molecule. This term HLB is described in "The HLB system. A time-saving guide to Eemulsifier selection" (published by ICI Americas Inc.; 1984).

In at least one embodiment, at least one aqueous composition (C) comprises no glycerolated surfactants.

The amount of at least one surfactant in the at least one aqueous composition (C) as an oil-in-water emulsion may range from 0.1% to 50% by weight, for example from 0.5% to 30% by weight, relative to the weight of the emulsion.

According to at least one embodiment, when the at least one aqueous composition (C) is a direct emulsion, it may be prepared by conventional processes for preparing direct emulsions, but also by a PIT process. The at least one aqueous composition (C) as a direct emulsion is, for example, prepared by a PIT process.

According to this embodiment, the principle of emulsification by phase inversion temperature (PIT) is, in its principle, described in 1968 by K. Shinoda (J. Chem. Soc. Jpn., 1968, 89, 435). It has been shown that this emulsification technique allows stable, fine emulsions to be obtained (K. Shinoda and H. Saito, J. Colloid Interface Sci., 1969, 30, 258). This technology is further described in "Application of the phase-inversion-temperature method to the emulsification of cosmetics"; T. Mitsui, Y. Machida and F. Harusawa, American Cosmet. Perfum., 1972, 87, 33.

A description of this technique is as follows: a mixture is prepared from an aqueous phase and an oily phase, and is brought to a temperature above the PIT temperature, the phase inversion temperature of the system, which is the temperature at which the equilibrium between the hydrophilic and lipophilic properties of the emulsifier(s) used is attained; at elevated temperature, in other words above the phase inversion temperature (>PIT), the emulsion is a water-in-oil emulsion, and, in the course of its cooling, this emulsion inverts at the phase inversion temperature, to become an oil-in-water emulsion, doing so by passing beforehand through a microemulsion state. This process makes it possible to obtain emulsions with a diameter of less than 4 µm.

According to this PIT process, the at least one aqueous composition (C) as a direct emulsion (oil-in-water emulsion) comprises at least 25% of at least one fat, including at least one oil, at least one surfactant, at least one of which is a nonionic surfactant exhibiting a cloud point, and an amount of water greater than 5% by weight, of the total weight of the emulsion. According to this embodiment, the nonionic surfactant has an HLB ranging from 8 to 18. The at least one surfactant may be chosen from oxyalkylenated surfactants, for example oxyethylenated surfactants, such as ethoxylated fatty alcohols, ethoxylated fatty acids, ethoxylated partial fatty acid glycerides, polyglycerolated triglycerides of fatty acids, and ethoxylated derivatives thereof, and mixtures of these. Moreover, an emulsion of this kind has a particle size of less than 4 for example less than 1 µm.

In greater detail, it is possible to operate as follows in order to obtain a PIT emulsion:

1) Weigh out into a container all of the constituents of the at least one aqueous composition (C) as a direct emulsion.

2) Homogenize the mixture, using for example a Rayneri blender of 350 rpm, and heat by gradually increasing the temperature using a water bath, up to a temperature greater than the phase inversion temperature T1, in other words until a transparent or translucent phase is obtained (microemulsion zone or lamellar phase) and then until a more viscous phase is obtained, which indicates that the inverse emulsion (W/0) has been obtained.

3) Stop the heating but continue stirring until ambient temperature has been regained, passing through the phase inversion temperature (T1), in other words the temperature at which a fine O/W emulsion is formed.

4) When the temperature has fallen below the phase inversion temperature (T1) zone again, add any additives and the heat-sensitive starting materials.

A stable final composition may be obtained wherein the lipophilic-phase droplets are fine, with sizes ranging from 10 to 200 nm.

In the zone where a microemulsion is formed (translucent mixture), the hydrophilic and hydrophobic interactions are balanced, since the surfactant has a tendency to form both direct micelles and inverse micelles. By heating beyond this zone, a W/O emulsion may be formed, because the surfactant promotes the formation of a water-in-oil emulsion. Subsequently, on cooling below the phase inversion zone, the emulsion becomes a direct emulsion (O/W).

Emulsification by phase inversion is explained in detail in the publication by T. Förster, W. von Rybinski, A. Wadle, Influence of microemulsion phases on the preparation of fine disperse emulsions, Advances in Colloid and Interface Sciences, 58, 119-149, 1995, which is cited here for reference.

The at least one oxidizing agent may also comprise other ingredients which are conventionally employed in the art, such as, in particular, those detailed above in the context of the least one substantially anhydrous or aqueous compositions (A) and (B).

According to at least one embodiment of the present disclosure, the amount of at least one oxidizing agent relative to the amount of at least one substantially anhydrous or aqueous compositions (A) and (B) is such that the amount of compound(s) of formula (I) ranges from 2% to 8% by weight in the final composition, in other words the composition resulting from the mixing of the at least one substantially anhydrous or aqueous composition (A), at least one substantially anhydrous or aqueous composition (B) and at least one aqueous composition (C); this mixing is carried out for example before application to the keratin fibers (extemporaneous preparation).

The at least one oxidizing agent may further comprise adjuvants such as those described in the context of the definitions of at least one substantially anhydrous or aqueous compositions (A) and (B), within the ranges of amounts that were previously described.

According to at least one embodiment, a composition comprising at least one dye precursor before mixing and the final ready-to-use composition with at least one oxidizing agent comprise at least one cationic polymer whose cationic charge density is greater than or equal to 4 milliequivalents per gram (meq./g), for example greater than or equal to 5 milliequivalents per gram (meq./g), further for example ranging from 5 to 20 meq./g and even further for example from 5.5 to 10 meq./g.

The cationic charge density of a polymer corresponds to the number of moles of cationic charges per unit mass of polymer under conditions in which it is totally ionized. It may be determined by calculation if the structure of the polymer is known, i.e. the structure of the monomers constituting the polymer and their mole proportion or weight proportion. It may also be determined experimentally via the Kjeldahl method, generally at a pH of about 7 at room temperature.

The at least one cationic polymer with a cationic charge density of greater than 4 meq./g may be chosen from any polymer known per se as improving the cosmetic properties of hair treated with compositions, for example, those described in patent application EP-A-0 337 354 and in French patent applications FR-A-2 270 846, 2 383 660, 2 598 611, 2 470 596 and 2 519 863.

In general, the term "cationic polymer" is presently understood in the context of the present disclosure to meanany polymer comprising cationic groups and/or groups that may be ionized into cationic groups.

The at least one cationic polymer is chosen from those comprising units comprising primary, secondary, tertiary and/or quaternary amine groups that either may form part of the main polymer chain or may be borne by a side substituent directly attached thereto.

The at least one cationic polymer used generally have a number-average molecular mass of ranging from approximately 500 to approximately $5 \times 10^6$ for example from approximately $10^3$ to approximately $3 \times 10^6$.

Among the at least one cationic polymer non-limiting mention may be made of, for example, polymers of the polyamine, polyamino amide and polyquaternary ammonium type.

Among the at least one cationic polymer, non-limiting mention may be made of, for example:

(1) homopolymers or copolymers derived from acrylic or methacrylic esters or amides and comprising at least one of the units of the following formulae:

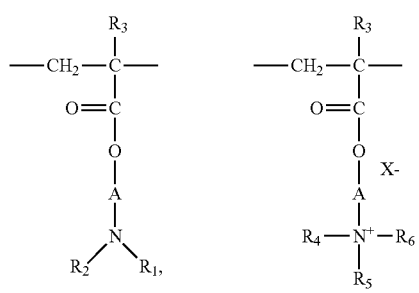

-continued

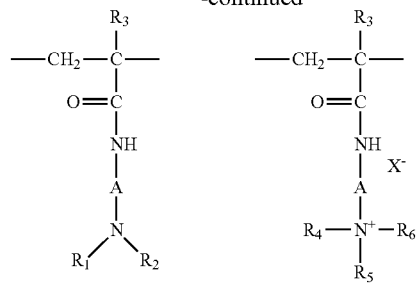

wherein:

$R_3$, which may be identical or different, is chosen from a hydrogen atom and a $CH_3$ radical;

A, which may be identical or different, is chosen from a linear or branched alkyl group of 1 to 6 carbon atoms, for example 2 or 3 carbon atoms, and a hydroxyalkyl group of 1 to 4 carbon atoms;

$R_4$, $R_5$ and $R_6$, which may be identical or different, are chosen from an alkyl group comprising from 1 to 18 carbon atoms and a benzyl radical for example, an alkyl group comprising from 1 to 6 carbon atoms;

$R_1$ and $R_2$, which may be identical or different, are chosen from a hydrogen and an alkyl group comprising from 1 to 6 carbon atoms, for example methyl or ethyl;

$X^-$ is an anion derived from a mineral or organic acid, such as a methosulfate anion or a halide such as chloride or bromide.

The copolymers of family (1) can also compriseat least one unit derived from comonomers that may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these copolymers of family (1), non-limiting mention may be made of, for example:

copolymers of acrylamide and of dimethylaminoethyl methacrylate quaternized with dimethyl sulfate or with a dimethyl halide, the copolymers of acrylamide and of methacryloyloxyethyltrimethylammonium chloride described, for example, in patent application EP-A-080 976, the copolymers of acrylamide and of methacryloyloxyethyltrimethylammonium methosulfate, quaternized or non-quaternized vinylpyrrolidone/dialkylaminoalkyl acrylate or methacrylate copolymers. These polymers are described in detail in French patents 2 077 143 and 2 393 573, dimethylaminoethyl methacrylate/vinylcaprolactam/vinylpyrrolidone terpolymers, vinylpyrrolidone/methacrylamidopropyldimethylamine copolymers, quaternized vinylpyrrolidone/dimethylaminopropylmethacrylamide copolymers, and crosslinked polymers of methacryloyloxy($C_1$-$C_4$) alkyltri($C_1$-$C_4$)alkylammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, for example, methylenebisacrylamide. A crosslinked acrylamide/methacryloyloxyethyltrimethylammonium chloride copolymer (20/80 by weight) in the form of a dispersion comprising 50% by weight of the said copolymer in mineral oil may be used. This dispersion is sold under the name SALCARE® SC 92 by the company Ciba. A crosslinked methacryloyloxyethyltrimethylammonium chloride homopolymer comprising about 50% by weight of the homopolymer in mineral oil or in a liquid ester can also be used. These dispersions are sold under the names SALCARE® SC 95 and SALCARE® SC 96 by the company Ciba.

(2) cyclopolymers of alkyldiallylamine or of dialkyldiallylammonium, such as the homopolymers or copolymers comprising, as main constituent of the chain, units corresponding to formula (VIII) or (IX):

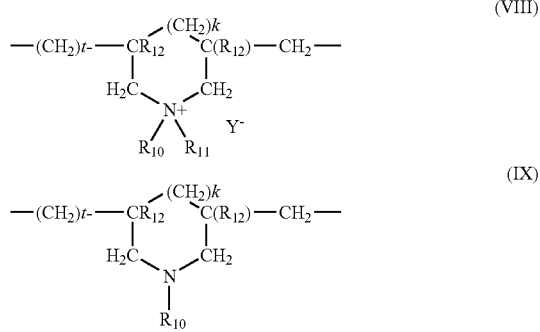

wherein formula k and t are integers chosen from 0 and 1, the sum of k+t being equal to 1; $R_{12}$ is chosen from a hydrogen atom and a methyl radical; $R_{10}$ and $R_{11}$, independently of each other, are chosen from an alkyl group comprising from 1 to 6 carbon atoms, a hydroxyalkyl group in which the alkyl group comprises, for example 1 to 5 carbon atoms, a lower ($C_1$-$C_4$) amidoalkyl group, or $R_{10}$ and $R_{11}$ may form, together with the nitrogen atom to which they are attached, heterocyclic groups such as piperidyl or morpholinyl; $Y^-$ is an anion such as bromide, chloride, acetate, borate, citrate, tartrate, bisulfate, bisulfite, sulfate or phosphate. These polymers are described in French patent 2 080 759 and in its Certificate of Addition 2 190 406.

In one embodiment, $R_{10}$ and $R_{11}$, independently of each other, may be, for example, an alkyl group comprising from 1 to 4 carbon atoms.

Among the polymers defined above, non-limiting mention may be made for example of the dimethyldiallylammonium salt, for example chloride, homopolymers sold under the name MERQUAT 100 by the company Nalco (and its homologues of low weight-average molar mass) and copolymers of diallyldimethylammonium chloride and of acrylamide.

(3) quaternary copolymers of vinyllactam (vinylpyrrolidone and/or vinylcaprolactam) and of vinylimidazole.

(4) the quaternary diammonium polymer comprising repeating units corresponding to the formula:

wherein in formula (X):

$R_{13}$, $R_{14}$, $R_{15}$ and $R_{16}$, which may be identical or different, are chosen from aliphatic, alicyclic or arylaliphatic radicals comprising from 1 to 20 carbon atoms or lower $C_1$-$C_6$ hydroxyalkylaliphatic radicals, or alternatively $R_{13}$, $R_{14}$, $R_{15}$ and $R_{16}$, together or separately, form, with the nitrogen atoms to which they are attached, heterocycles optionally comprising a second heteroatom other than nitrogen, or alternatively $R_{13}$, $R_{14}$, $R_{15}$ and $R_{16}$ are chosen from a linear or branched $C_1$-$C_6$ alkyl radical substituted with a nitrile, ester, acyl or amide group or a group —CO—O—$R_{17}$-D or —CO—NH—$R_{17}$-D where $R_{17}$ is an alkylene and D is a quaternary ammonium group;

$A_1$ and $B_1$ are chosen from polymethylene groups comprising from 2 to 20 carbon atoms, which groups may be linear or branched, saturated or unsaturated, and which may comprise, linked to or intercalated in the main chain, at least one aromatic ring or at least one oxygen or sulfur atom or sulfoxide, sulfone, disulfide, amino, alkylamino, hydroxyl, quaternary ammonium, ureido, amide or ester groups, and $X^-$ is an anion derived from a mineral or organic acid;

$A_1$, $R_{13}$ and $R_{15}$ may form, with the two nitrogen atoms to which they are attached, a piperazine ring; in addition, if A1 is a linear or branched, saturated or unsaturated alkylene or hydroxyalkylene radical, $B_1$ can also be a group $(CH_2)_n$—CO-D-OC—$(CH_2)_p$— wherein:

n and p, which may be identical or different, are integers ranging from approximately 2 to approximately 20, D is chosen from:

a) a glycol residue of formula: —O—Z—O—, wherein Z is chosen from a linear or branched hydrocarbon-based radical or a group corresponding to one of the following formulae:

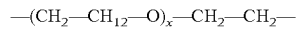

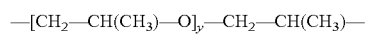

wherein x and y are chosen from an integer ranging from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y is chosen from a linear or branched hydrocarbon-based radical, or alternatively the divalent radical —CH$_2$—CH$_2$—S—S—CH$_2$—CH$_2$—;

d) a ureylene group of formula: —NH—CO—NH—.

For example, $X^-$ is an anion such as chloride or bromide.

In one embodiment, polymers may have a number-average molecular mass ranging from 1 000 and 100 000.

Polymers, for example, are described in French Patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is further possible to use polymers that are formed from repeating units corresponding to the formula:

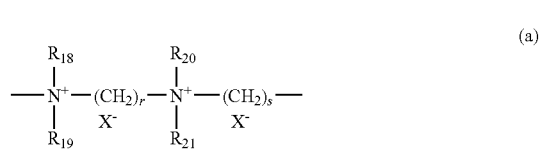

wherein $R_{18}$, $R_{19}$, $R_{20}$ and $R_{21}$, which may be identical or different, are chosen from an alkyl or hydroxyalkyl radical comprising from approximately 1 to approximately 4 carbon atoms, r and s are integers ranging from approximately 2 to approximately 20, and X— is an anion derived from a mineral or organic acid.

For example, one compound of formula (a) is the one for which $R_{18}$, $R_{19}$, $R_{20}$ and $R_{21}$ are a methyl radical and r is 3, s is 6 and X is Cl, which is known as Hexadimethrine chloride according to the INCI (CTFA) nomenclature.

(5) polyquaternary ammonium polymers comprising units of formula (XI):

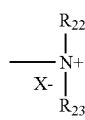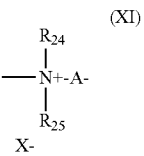

wherein:

$R_{22}$, $R_{23}$, $R_{24}$ and $R_{25}$, which may be identical or different, are chosen from a hydrogen atom and a methyl, ethyl, propyl, β-hydroxyethyl, β-hydroxypropyl and —CH$_2$CH$_2$(OCH$_2$CH$_2$)$_p$OH radical, where p is equal to 0 or to an integer ranging from 1 to 6, with the proviso that $R_{22}$, $R_{23}$, $R_{24}$ and $R_{25}$ are not simultaneously a hydrogen atom, t and u, which may be identical or different, are integers ranging from 1 to 6, v is equal to 0 or to an integer ranging from 1 to 34, $X^-$ is an anion such as a halide, A is a dihalide radical or is —CH$_2$—CH$_2$—O—CH$_2$—CH$_2$—.

Such compounds are described in patent application EP-A-122 324.

Examples may include, for example the products MIRAPOL® A15, MIRAPOL® AD1, MIRAPOL® AZ1 and MIRAPOL® 175 sold by the company Miranol.

Other cationic polymers that may be used in the context of the present disclosure are polyalkyleneimines, for example polyethyleneimines, polymers comprising vinylpyridine or vinylpyridinium units, condensates of polyamines and of epichlorohydrin, quaternary polyureylenes and chitin derivatives.

Among the at least one cationic polymer that may be used in the context of the present disclosure, non-limiting mention made be made of cationic cyclopolymers, for example, the dimethyldiallylammonium chloride homopolymers sold under the name MERQUAT 100 by the company Nalco (and its homologues of low weight-average molar mass), and polyethyleneimines, and mixtures thereof.

According to the disclosure herein, the at least one cationic polymer with a cationic charge density of greater than or equal to 4 meq./g may range from 0.001% to 10% by weight, for example from 0.005% to 5% by weight and further for example from 0.01% to 3% by weight relative to the total weight of the final ready-to-use composition comprising the at least one dye precursor before mixing.

According to another embodiment, the composition comprising the at least one dye precursor before mixing and the final ready-to-use composition with the at least one oxidizing agent also comprise at least one nonionic oxyalkylenated or glycerolated surfactant as defined previously.

In accordance with at least one embodiment of the disclosure, the composition comprises at least one nonionic surfactant chosen from oxyalkylenated and glycerolated $C_6$-$C_{30}$ alcohols.

According to another embodiment of the dislcosure described above, the total amount of oxyalkylenated or glycerolated nonionic surfactants range from 0.01% to 50% by weight, for example from 0.1% to 30% by weight, for example 0.1% to 20% and further for example from 0.1% to 10% by weight relative to the weight of the final ready-to-use composition or of the composition comprising the at least one dye precursor before mixing.

Hence a method according to an embodiment of the disclosure is implemented by applying a composition obtained by extemporaneous mixing, at the time of use, of the three compositions to the dry or wet keratin fibers.

The weight ratio R1 of the amounts of compositions (A)+(B)/(C) and the weight ratio R2 of the compositions (A)/(B) range from 0.1 to 10 for example from 0.3 to 5.

According to at least one embodiment, the weight ratio of the amounts of compositions (C)/(A)+(B)+(C) ranges from 0.4 to 0.7.

The mixture on the fibers is left in place for a time ranging from 1 minute to 1 hour, for example ranging from 10 minutes to 30 minutes.

The temperature during the method ranges from the ambient temperature (between 15 to 25° C.) to 80° C., for example from ambient temperature to 60° C.

At the end of the treatment, the human keratin fibers are optionally rinsed with water, washed with shampoo, rinsed again with water, and then dried or left to dry.

As indicated previously, one embodiment of the disclosure is a ready-to-use composition comprising at least one organosilicon compound as defined previously and at least one dye precursor, at least one oxidizing agent and at least one cationic polymer and/or at least one oxyalkylenated or glycerolated nonionic surfactant. This composition may further comprise at least one alkaline agent other than the organosilicon compounds.

The ready-to-use dye composition may be in various forms, such as in the form of liquids, creams or gels, or in any other form that is suitable for dyeing the hair.

A multiple-compartment device is also disclosed herein, comprising in a first compartment at least one substantially anhydrous or aqueous composition (A) comprising at least one fat free of carboxylic acid groups and at least one surfactant, in a second compartment at least one substantially anhydrous or aqueous composition (B) comprising at least one compound of formula (I) and in a third compartment at least one aqueous composition (C) comprising at least one oxidizing agent.

As disclosed herein, the percentages stated are by weight.

Other than in the examples, or where otherwise indicated, all numbers expressing quantities of ingredients, reaction conditions, and so forth used in the specification and claims are to be understood as being modified in all instances by the term "about" Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow are intended to illustrate the present disclosure without, however, being limiting in nature.

EXAMPLES

Example 1

Lightening Composition

The following compositions were prepared:
Anhydrous Composition A (Percentages Expressed in g %):

| | |
|---|---|
| Propylene carbonate | 1 |
| Octyldodecanol | 11.5 |
| Glycol distearate | 8 |
| Laureth-2 | 1 |
| Polysorbate 21 | 11 |
| Disteardimonium hectorite | 3 |
| Liquid paraffin | qs 100 g |

Anhydrous Composition B (Percentages Expressed in q %):

| | |
|---|---|
| Ethyl alcohol | 38.2 |
| Hexylene glycol | 12.9 |
| Dipropylene glycol | 12.9 |
| (3-Aminopropyl)triethoxysilane (*) | 36 |

(*): 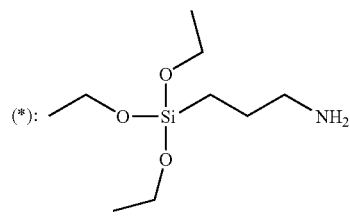

Oxidizing Composition C (Percentages Expressed in q %):

| | |
|---|---|
| Tocopherol | 0.1 |
| Sodium stannate | 0.04 |
| Pentasodium pentetate | 0.06 |
| Polyquaternium-6 | 0.2 |
| Glycerol | 0.5 |
| Ceteareth-33 | 3 |
| Cetearyl alcohol | 8 |
| Hexadimethrine chloride | 0.15 |
| Ceteareth-33 | 3 |
| Phosphoric acid | qs pH = 2.2 |
| Hydrogen peroxide | 6 |
| Tetrasodium pyrophosphate | 0.03 |
| Liquid paraffin | 20 |
| Protected ethoxylated (4EO) rapeseed acid amide | 1.20 |
| Demineralized water | qs 100 g |

At the time of use, 10 g of composition (A) was mixed with 4 g of composition (B) and 20 g of composition (C).

The resulting mixture (pH=9.8±0.1) was applied to a lock of relaxed hair with a tone depth of 4.

NB: Relaxing was carried out using the product Dark and Lovely Super (from Softsheen Carson) for 20 minutes at 27° C. on a hot plate. The relaxing product/lock ratio is 10/1 (weight/weight) respectively. At the end of the treatment, the hair was rinsed with water, washed with the shampoo Color Signal Neutralizing Shampoo (Dark and Lovely), and then rinsed with water and dried.

The time for which the mixture of compositions (A), (B) and (C) was left on the relaxed hair was 30 minutes at 27° C. on a hot plate.

At the end of this leave-in time, the lock was washed with Elvive Multivitamin shampoo, then dried under a hood at 60° C.

The coloring of the locks was measured using a Konica Minolta CM2600D colorimeter (10° observer, D65 illuminant).

As shown in the table below, a good level of lightening was obtained.

Moreover, the lock had a soft and smooth cosmetic feel.

Finally, application was pleasant, with no sharp odor.

| | L* | a* | b* | ΔE*ab |
|---|---|---|---|---|
| Relaxed brown hair, untreated | 17.65 | 1.88 | 1.96 | |
| Hair treated with the mixture of the invention | 18.32 | 4.84 | 5.21 | 4.44 |

Example 2

Coloring Composition

The following compositions were prepared:
Anhydrous Composition (A) (Percentages Expressed in g %):

| | |
|---|---|
| Propylene carbonate | 1 |
| Octyldodecanol | 11.5 |
| Glycol distearate | 8 |
| Laureth-2 | 1 |
| Polysorbate 21 | 11 |
| Disteardimonium hectorite | 3 |
| Liquid paraffin | qs 100 g |

Anhydrous Composition (B) (Percentages Expressed in q %):

| | |
|---|---|
| Pure denatured ethyl alcohol | 8.8 |
| Hexylene glycol | 3 |
| Dipropylene glycol | 3 |
| (3-Aminopropyl)triethoxysilane | 36 |
| Ceteareth-33 | 21.25 |
| para-Phenylenediamine | 0.33 |
| 2-Methyl-5-hydroxyethylaminophenol | 4.08 |
| 5-Amino-6-chloro-o-cresol | 2.72 |
| para-Aminophenol | 3.4 |
| Ascorbyl palmitate | 0.2 |
| Condensate of ethylene oxide and propylene oxide and ethylene oxide MW: 2900 g/mol; 13EO/30PO/13EO | qs 100 |

Oxidizing Composition (C) (Percentages Expressed in q %):

| | |
|---|---|
| Tocopherol | 0.1 |
| Sodium stannate | 0.04 |
| Pentasodium pentetate | 0.06 |
| Polyquaternium-6 | 0.2 |
| Glycerol | 0.5 |
| Cetearyl alcohol | 8 |
| Hexadimethrine chloride | 0.15 |
| Ceteareth-33 | 3 |
| Phosphoric acid | 0 |
| Hydrogen peroxide | 6 |
| Tetrasodium pyrophosphate | 0.03 |
| Liquid paraffin | 20 |
| Protected ethoxylated (4 EO) rapeseed acid amide | 1.20 |
| Demineralized water | qs 100 g |

At the time of use, 10 g of composition (A) was mixed with 4 g of composition (B) and 20 g of composition (C).

The resulting mixture (pH=9.8±0.1) was applied to a lock of natural hair with a grey hair content of 90%.

The time for which the mixture of compositions (A), (B) and (C) was left on the hair was 30 minutes at 27° C. on a hot plate.

At the end of this leave-on time, the lock was washed with Elvive Multivitamin shampoo, then dried under a hood at 60° C.

The coloring of the locks was measured using a Konica Minolta CM2600D colorimeter (10° observer, D65 illuminant).

As shown in the table below, a coppery red color was obtained, with good covering of the grey hair.

| | L* | a* | b* | ΔE*ab |
|---|---|---|---|---|
| Natural hair with 90% grey hairs (NG) | 60.41 | 0.35 | 15.41 | — |
| NG treated with the mixture of the invention | 16.71 | 30.85 | 28.54 | 54.89 |

Example 3

Lightening Composition

The following compositions were prepared:
Anhydrous Composition A1 (Percentages Expressed in q %):

| | |
|---|---|
| Propylene carbonate | 1 |
| Octyldodecanol | 11.5 |
| Glycol distearate | 8 |
| Laureth-2 | 1 |
| Polysorbate 21 | 11 |
| Disteardimonium hectorite | 3 |
| Liquid paraffin oil | qs 100 g |

Aqueous Composition B1 (Percentages Expressed in q %):

| | |
|---|---|
| Ethyl alcohol | 8.8 |
| Hexylene glycol | 3 |
| Propylene glycol | 6.2 |
| Dipropylene glycol | 3 |
| Diethylenetriaminepentaacetic acid at 40% in water | 1 |
| Ascorbic acid | 0.25 |

-continued

| | |
|---|---|
| Sodium metal bisulfite | 0.7 |
| (3-Aminopropyl)triethoxysilane (*) | 10.87 |
| Pure methanolamine | 15.05 |
| Demineralized water | qs 100 |

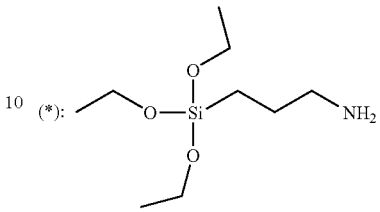

(*):

Oxidizing Composition (C1) (Percentages Expressed in q %):

Emulsion A (Prepared by the PIT process)

| Phase 1 | Crystalline sorbitol | 5 |
|---|---|---|
| | Liquid paraffin oil | 60.2 |
| | Demineralized water | 16.625 |
| | Oxyethylenated 10 OE behenyl alcohol | 6 |
| | Phosphoric acid | 0.15 |
| Phase II | Etidronic acid, tetrasodium salt, as an aqueous 30% solution | 0.2 |
| | Tetrasodium pyrophosphate decahydrate | 0.04 |
| | Sodium salicylate | 0.035 |
| | Tetramethylhexamethylenediamine/1,3-dichloropropylene polycondensate as an aqueous solution | 0.25 |
| | Polydimethyldiallylammonium chloride at 40% in water, non-stabilized | 0.5 |
| | Denatured 96° ethyl alcohol | 2 |
| | Condensate of ethylene oxide and propylene oxide and ethylene oxide. MW: 2900 g/mol; 13 OE/30 OP/13 OE | 3 |
| Phase III | Hydrogen peroxide | 6 |

Process for Manufacturing the Emulsion

The ingredients of phase I were heated on a water bath with stirring of Rayneri type (400 rpm). A fluid white emulsion that becomes translucent at about 68° C. and thickens thereabove was obtained.

Once the emulsion was thickened, the water bath was removed and the mixture was allowed to cool with continued stirring At 40° C., the ingredients of phase II were introduced Finally, the hydrogen peroxide was introduced The weight loss of water was compensated for (<5%)

The emulsion obtained was a thick cream of pH=3

Application of the Composition

At the time of use, 10 g of composition (A1) was mixed with 4 g of composition (B1) and 15 g of composition (C1).

The mixture obtained (pH=10±0.1) was applied to a lock of relaxed hair with a tone depth of 4.

It should be noted that the relaxing was performed with the product Dark and Lovely Super (from Softsheen Carson) for 20 minutes at 27° C. on a hot plate. The relaxing product/lock ratio is 10/1 (weight/weight), respectively. After the treatment, the hair was rinsed with water, washed with the shampoo Color Signal Neuralizing Shampoo (Dark and Lovely) and then rinsed with water and dried.

The leave-on time of the mixture of compositions (A1), (B1) and (C1) on the relaxed hair was 30 minutes at 27° C. on a hot plate.

After this leave-on time, the lock was washed with Elvive multivitamin shampoo and then dried under a hood at 60° C.

Results

The coloration of the locks was measured using a Konica Minolta CM 2600D colorimeter (10° observer, illuminant D65).

As shown in the table below, a good level of lightening was obtained.

In addition, the lock had a soft, smooth cosmetic feel.

Finally, the application was pleasant since there was no noxious odor.

|  | L* | a* | b* | ΔE*ab |
|---|---|---|---|---|
| Relaxed chestnut-brown hair | 17.54 | 1.92 | 1.83 | / |
| Hair treated with the mixture of the invention | 20.25 | 5.48 | 6.07 | 6.17 |

Example 4

Dye Composition

The compositions below were prepared:
Anhydrous Composition (A2) (Percentages Expressed in q %):

| Propylene carbonate | 1 |
|---|---|
| Octyldodecanol | 11.5 |
| Glycol distearate | 8 |
| Laureth-2 | 1 |
| Polysorbate 21 | 11 |
| Disteardimonium hectorite | 3 |
| Liquid paraffin oil | qs 100 g |

Anhydrous Composition (B2) (Percentages Expressed in g %):

| Denatured ethyl alcohol | 8.8 |
|---|---|
| Hexylene glycol | 3 |
| Propylene glycol | 6.2 |
| Dipropylene glycol | 3 |
| Diethylenetriaminepentaacetic acid at 40% in water | 1 |
| Ascorbic acid | 0.25 |
| Sodium metabisulfite | 0.7 |
| (3-Aminopropyl)triethoxysilane | 10.87 |
| Pure monoethanolamine | 15.05 |
| para-Phenylenediamine | 0.28 |
| para-Aminophenol | 3.48 |
| 1-Methyl-2-hydroxy-4-β-hydroxyethylaminobenzene | 2.9 |
| Purified 5-amino-6-chloro-o-cresol | 2.32 |
| Demineralized water | qs 100 g |

Oxidizing Composition (C2) (Percentages Expressed in q %):

| Tocopherol | 0.1 |
|---|---|
| Sodium stannate | 0.04 |
| Pentasodium pentetate | 0.06 |
| Polyquaternium-6 | 0.2 |
| Glycerol | 0.5 |
| Cetearyl alcohol | 8 |
| Hexadimethrine chloride | 0.15 |
| Ceteareth-33 | 3 |
| Phosphoric acid | 0 |
| Hydrogen peroxide | 6 |
| Tetrasodium pyrophosphate | 0.03 |
| Liquid paraffin oil | 20 |
| Protected oxyethylenated (4 OE) rapeseed acid amide | 1.20 |
| Demineralized water | qs 100 g |

Composition C2 was prepared by hot-mixing the water-insoluble compounds (fatty phase), followed by addition of the aqueous phase formed from the water and the water-soluble compounds.

Application of the Composition

At the time of use, 10 g of composition (A2) was mixed with 4 g of composition (B2) and 15 g of composition (C2).

The mixture obtained (pH=10.1±0.1) was applied to a lock of natural hair comprising 90% grey hairs.

The leave-on time of the mixture of compositions (A2), (B2) and (C2) was 30 minutes at 27° C. on a hot plate.

After this leave-on time, the lock was washed with Elvive multivitamin shampoo and then dried under a hood at 60° C.

Results

The coloration of the locks was measured using a Konica Minolta CM2600D colorimeter (10° observer, illuminant D65).

As shown in the table below, a coppery-red color was obtained, with good covering of the grey hair.

|  | L* | a* | b* | ΔE*ab |
|---|---|---|---|---|
| Natural hair comprising 90% grey hairs (NG) | 52.42 | 1.53 | 12.41 | / |
| NG treated with the mixture of the invention | 25.85 | 16.24 | 12.16 | 30.37 |

Example 5

Dye Composition

The following compositions were prepared (amount in grams of active material):

Aqueous composition comprising at least one organosilicon compound:

| Lactic acid | 10.8 |
|---|---|
| Hydroxyethylcellulose (NATROSOL 250 HHR from Aqualon) | 0.4 |
| 3-Aminopropyltriethoxysilane Dow Corning Z-6011 SILANE | 30 |
| Water | qs 100 |

Composition comprising oxidation dyes and an alkaline agent:

| Oleic acid | 2.7 |
|---|---|
| Ammonium hydroxide | 2.22 (expressed as NH₃) |
| Pentasodium pentetate | 0.8 |
| Monoetanolamine | 0.63 |
| 2-Oleamido-1,3-octadecanediol | 0.01 |
| 2,5-Diaminotoluene | 0.7623 |
| Resorcinol | 0.66 |
| m-Aminophenol | 0.14 |
| 2,4-Diaminophenoxyethanol 2HCl | 0.02 |
| Cetearyl alcohol | 16.2 |
| Oleyl alcohol | 2.7 |
| Hexadimethrine chloride (MEXOMERE PO from Chimex) | 3 |
| Oleth-30 | 3.6 |
| Sodium metabisulfite | 0.71 |

-continued

| | |
|---|---|
| Fragrance | 0.5 |
| Water | qs 100 |

Composition comprising aqueous hydrogen peroxide solution:

| | |
|---|---|
| Trideceth Carboxamide MEA | 0.85 |
| Sodium stannate | 0.04 |
| Pentasodium pentetate | 0.06 |
| Glycerol | 0.5 |
| Cetearyl alcohol | 2.28 |
| Ceteareth-25 | 0.57 |
| Hydrogen peroxide | 6 |
| Tetrasodium pyrophosphate | 0.02 |
| Phosphoric acid | qs pH 2 |
| Water | qs 100 |

The composition comprising oxidation dyes and an alkaline agent was diluted extemporaneously with one and a half times its weight of the composition comprising the oxidizing agent.

The aqueous composition comprising at least one organosilicon compound was introduced into the preceding mixture to a proportion of 6 grams per 120 grams of preceding mixture.

This mixture was then applied to fine chestnut-brown hair.

After a leave-on time of 30 minutes at room temperature, the hair was rinsed, washed with a standard shampoo and dried.

After bleaching and dyeing the hair, hair dyed in a light chestnut-brown shade was finally obtained. The head of hair had pronounced styling properties with a lot of volume, and had more body.

What is claimed is:

1. A method of coloring and/or lightening human keratin fibers, comprising contacting fibers with:
    at least one substantially anhydrous or aqueous composition (A) comprising at least one fat free of carboxylic acid groups and at least one surfactant;
    at least one substantially anhydrous or aqueous composition (B) comprising at least one aminotrialkoxysilane or aminotrialkenyloxysilane compound of formula (I) below:

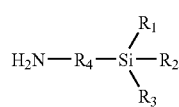
(I)

wherein:
    $R_1$, $R_2$ and $R_3$, which are identical or different, are chosen from:
        a linear or branched $C_1$-$C_{20}$ alkoxy radical wherein the alkyl moiety is optionally interrupted with at least one oxygen atom, and
        a linear or branched $C_2$-$C_{20}$ alkenyloxy radical;

$R_4$ is a divalent radical of structure:

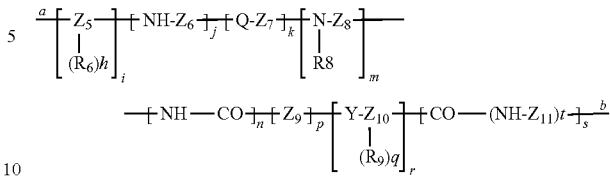

wherein:
    $R_6$, identical or different at each occurrence, is chosen from a linear or branched $C_1$-$C_4$ alkyl radical, optionally substituted with at least one hydroxyl group, an $NH_2$ radical, a hydroxyl radical, a cyano radical, a radical $Z_{12}NH_2$, a radical $Z_{13}NH\ Z_{14}NH_2$, and a linear or branched $C_2$-$C_{10}$ alkenyl radical, with $Z_{12}$, $Z_{13}$ and $Z_{14}$ being chosen from, independently of each other, a $C_1$-$C_{20}$, linear alkylene radical
    $R_8$ is chosen from a linear or branched $C_1$-$C_4$ alkyl radical, optionally substituted with at least one hydroxyl or carboxyl groups, a linear or branched $C_2$-$C_{10}$, alkenyl radical, a radical $Z_{15}NH_2$, a radical $Z_{16}R_8'$ and a radical $Z_{17}Si\ OSi(R_a)_2(R_b)$ wherein
    $R_a$ is a linear or branched $C_1$-$C_4$ alkoxy radical,
    $R_b$ is a linear or branched $C_1$-$C_4$ alkyl radical,
    $Z_{15}$, $Z_{16}$ and $Z_{17}$ are, independently of each other, a $C_1$-$C_{20}$ linear alkylene radical
    $R_8'$ is a $C_6$-$C_{30}$ aryl radical,
    $R_9$ is a linear or branched $C_1$-$C_4$ alkyl radical
    $Z_5$, $Z_6$, $Z_7$, $Z_8$, $Z_9$, $Z_{10}$ and $Z_{11}$ are, independently of each other, a $C_1$-$C_{20}$ linear alkylene radical
    Q is a saturated or unsaturated six-membered ring optionally comprising at least one heteroatom;
    Y, identical or different at each occurrence, is chosen from an oxygen atom, a sulfur atom and an NH group
    h is an integer chosen from 0, 1, 2, 3, 4 and 5
    i is an integer chosen from 0 and 1
    j is an integer chosen from 0, 1, 2 and 3
    k is an integer chosen from 0 and 1
    m is an integer chosen from 0 and 1
    n is an integer chosen from 0 and 1
    p is an integer chosen from 0 and 1
    q is an integer chosen from 0 and 1
    r is an integer chosen from 0, 1, 2 and 3
    s is an integer chosen from 0 and 1
    wherein at least one of the coefficients h, i, j, k, m, n, p, q, r and s is non-zero
    a is the bond to the silicon atom
    b is the bond to the nitrogen atom of the amino group; and
        at least one aqueous composition (C) comprising at least one oxidizing agent.

2. A method according to claim 1, wherein in the compound of formula (I), $R_1$ and $R_2$ are identical.

3. A method according to claim 1, wherein the compound of formula (I) comprises only one silicon atom.

4. A method according to claim 1, wherein in the compound of formula (I) $R_1$, $R_2$ and $R_3$ are identical.

5. A method according to claim 1, wherein in the compound of formula (I) t k, n and s are 0.

6. A method according to claim 1, wherein the at least one substantially anhydrous or aqueous composition (A) and/or the at least one substantially anhydrous or aqueous composition (B) further comprises at least one oxidation dye precursor chosen from at least one oxidation coupler, at least one oxidation base, at least one direct dye, and mixtures thereof.

7. A method according to claim 1, wherein the fat is a compound chosen from a fatty alcohol, a fatty acid ester, a fatty alcohol ester, a mineral, vegetable, animal or synthetic oil, a silicone and a wax.

8. A method according to claim 7, wherein the fat is chosen from liquid petrolatum, liquid paraffin, polydecenes, fatty acid esters and mixtures thereof.

9. A method according to claim 1, wherein, the at least one substantially anhydrous or aqueous composition (A) and/or the at least one substantially anhydrous or aqueous composition (B) further comprises an alkaline agent different from the compounds of formula (I).

10. A method according to claim 9, wherein the alkaline agent is chosen from organic amines with a pKb at 25° C. of less than 12 and salts thereof; inorganic bases possessing in their structure at least one element from columns 1 to 13 of the Periodic Table of the Elements, other than hydrogen, which do not simultaneously comprise carbon and hydrogen atoms; and ammonium salts chosen from the following acid salts: acetate, carbonate, bicarbonate, chloride, citrate, nitrate, nitrite, phosphate, and sulfate.

11. A method according to claim 9, wherein the alkaline agent is chosen from alkanolamines, basic amino acids, and alkali metal carbonates or hydroxides, and mixtures thereof.

12. A method according to claim 1, wherein prior to contacting the fibers, the method further comprises extemporaneous mixing of, at the time of use, the at least one substantially anhydrous or aqueous composition (A), the at least one substantially anhydrous or aqueous composition (B) and the at least one aqueous composition (C).

13. A ready-to-use composition comprising:
at least one dye precursor chosen from at least one oxidation coupler, at least one oxidation base, at least one direct dye, and mixtures thereof;
at least one aminotrialkoxysilane or aminotrialkenyloxysilane compound of formula (I) below:

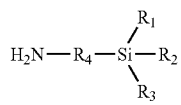

(I)

wherein:
$R_1$, $R_2$ and $R_3$, which are identical or different, are chosen from:
a linear or branched $C_1$-$C_{20}$ alkoxy radical wherein the alkyl moiety is optionally interrupted with at least one oxygen atom, and
a linear or branched $C_2$-$C_{20}$ alkenyloxy radical;
$R_4$ is a divalent radical of structure:

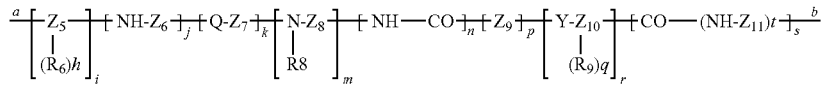

wherein:
$R_6$, identical or different at each occurrence, is chosen from a linear or branched $C_1$-$C_4$ alkyl radical, optionally substituted with at least one hydroxyl group, an $NH_2$ radical, a hydroxyl radical, a cyano radical, a radical $Z_{12}NH_2$, a radical $Z_{13}NH\ Z_{14}NH_2$, and a linear or branched $C_2$-$C_{10}$ alkenyl radical, with $Z_{12}$, $Z_{13}$ and $Z_{14}$ being chosen from, independently of each other, a $C_1$-$C_{20}$, linear alkylene radical
$R_8$ is chosen from a linear or branched $C_1$-$C_4$ alkyl radical, optionally substituted with at least one hydroxyl or carboxyl groups, a linear or branched $C_2$-$C_{10}$, alkenyl radical, a radical $Z_{15}NH_2$, a radical $Z_{16}R_8'$ and a radical $Z_{17}Si\ OSi(R_a)_2(R_b)$ wherein
$R_a$ is a linear or branched $C_1$-$C_4$ alkoxy radical,
$R_b$ is a linear or branched $C_1$-$C_4$ alkyl radical,
$Z_{15}$, $Z_{16}$ and $Z_{17}$ are, independently of each other, a $C_1$-$C_{20}$ linear alkylene radical
$R_8'$ is a $C_6$-$C_{30}$ aryl radical,
$R_9$ is a linear or branched $C_1$-$C_4$ alkyl radical
$Z_5$, $Z_6$, $Z_7$, $Z_8$, $Z_9$, $Z_{10}$ and $Z_{11}$ are, independently of each other, a $C_1$-$C_{20}$ linear alkylene radical
Q is a saturated or unsaturated six-membered ring optionally comprising at least one heteroatom;
Y, identical or different at each occurrence, is chosen from an oxygen atom, a sulfur atom and an NH group
h is an integer chosen from 0, 1, 2, 3, 4 and 5
i is an integer chosen from 0 and 1
j is an integer chosen from 0, 1, 2 and 3
k is an integer chosen from 0 and 1
m is an integer chosen from 0 and 1
n is an integer chosen from 0 and 1
p is an integer chosen from 0 and 1
q is an integer chosen from 0 and 1
r is an integer chosen from 0, 1, 2 and 3
s is an integer chosen from 0 and 1
wherein at least one of the coefficients h, i, j, k, m, n, p, q, r and s is non-zero
a is the bond to the silicon atom
b is the bond to the nitrogen atom of the amino group;
at least one cationic polymer whose cationic charge density is greater than or equal to 4; and
at least one polyoxyalkylenated or glycerolated nonionic surfactant.

14. A composition according to claim 13, further comprising at least one alkaline agent different from the compounds of formula (I).

15. A multiple-compartment device comprising in a first compartment at least one substantially anhydrous or aqueous composition (A) comprising at least one fat free of carboxylic acid groups and at least one surfactant; in a second compartment at least one substantially anhydrous or aqueous composition (B) comprising at least one compound of the formula (I); and in a third compartment at least one aqueous composition (C) comprising at least one oxidizing agent; formula (I) comprising as follows:

(I)

wherein:
$R_1$, $R_2$ and $R_3$, which are identical or different, are chosen from:
a linear or branched $C_1$-$C_{20}$ alkoxy radical wherein the alkyl moiety is optionally interrupted with at least one oxygen atom,
a linear or branched $C_2$-$C_{20}$ alkenyloxy radical, $R_4$ is a divalent radical of structure:

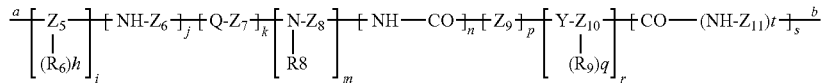

wherein:

- $R_6$, identical or different at each occurrence, is chosen from a linear or branched $C_1$-$C_4$ alkyl radical, optionally substituted with at least one hydroxyl group, an $NH_2$ radical, a hydroxyl radical, a cyano radical, a radical $Z_{12}NH_2$, a radical $Z_{13}NH\ Z_{14}NH_2$, a linear or branched $C_2$-$C_{10}$ alkenyl radical, with $Z_{12}$, $Z_{13}$ and $Z_{14}$ being chosen from, independently of each other, a $C_1$-$C_{20}$ linear alkylene radical
- $R_8$ is chosen from a linear or branched $C_1$-$C_4$ alkyl radical, optionally substituted with at least one hydroxyl or carboxyl groups, a linear or branched $C_2$-$C_{10}$ alkenyl radical, a radical $Z_{15}NH_2$, a radical $Z_{16}R_8'$ and a radical $Z_{17}Si\ OSi(R_a)_2(R_b)$ where
- $R_a$ is a linear or branched $C_1$-$C_4$ alkoxy radical,
- $R_b$ is a linear or branched $C_1$-$C_4$ alkyl radical,
- $Z_{15}$, $Z_{16}$ and $Z_{17}$ are, independently of each other, a $C_1$-$C_{20}$ linear alkylene radical
- $R_8'$ is a $C_6$-$C_{30}$ aryl radical,
- $R_9$ is a linear or branched $C_1$-$C_4$ alkyl radical
- $Z_5$, $Z_6$, $Z_7$, $Z_8$, $Z_9$, $Z_{10}$ and $Z_{11}$ are, independently of each other, a $C_1$-$C_{20}$ linear alkylene radical
- Q is a saturated or unsaturated six-membered ring optionally comprising at least one heteroatoms
- Y, identical or different at each occurrence, is chosen from an oxygen atom, a sulfur atom and an NH group
- h is an integer chosen from 0, 1, 2, 3, 4 and 5
- i is an integer chosen from 0 and 1
- j is an integer chosen from 0, 1, 2 and 3
- k is an integer chosen from 0 and 1
- m is an integer chosen from 0 and 1
- n is an integer chosen from 0 and 1
- p is an integer chosen from 0 and 1
- q is an integer chosen from 0 and 1
- r is an integer chosen from 0, 1, 2 and 3
- s is an integer chosen from 0 and 1
- wherein at least one of the coefficients h, i, j, k, m, n, p, q, r and s is non-zero
- a is the bond to the silicon atom
- b is the bond to the nitrogen atom of the amino group.

* * * * *